(12) United States Patent
Cao

(10) Patent No.: US 6,929,472 B2
(45) Date of Patent: Aug. 16, 2005

(54) CURING LIGHT

(75) Inventor: Densen Cao, Sandy, UT (US)

(73) Assignee: Cao Group, Inc., Sandy, UT (US)

( * ) Notice: Subject to any disclaimer, the term of this patent is extended or adjusted under 35 U.S.C. 154(b) by 383 days.

(21) Appl. No.: 10/072,462

(22) Filed: Feb. 5, 2002

(65) Prior Publication Data

US 2002/0172913 A1 Nov. 21, 2002

Related U.S. Application Data

(63) Continuation-in-part of application No. 10/016,992, filed on Dec. 13, 2001, which is a continuation-in-part of application No. 09/405,373, filed on Sep. 24, 1999, now Pat. No. 6,331,111, said application No. 10/072,462, is a continuation-in-part of application No. 10/017,272, filed on Dec. 13, 2001, now Pat. No. 6,783,362, said application No. 10/072,462, is a continuation-in-part of application No. 10/017,454, filed on Dec. 13, 2001, said application No. 10/072,462, is a continuation-in-part of application No. 10/017,455, filed on Dec. 13, 2001.

(60) Provisional application No. 60/304,324, filed on Jul. 10, 2001.

(51) Int. Cl.[7] .......................... A61C 19/00; H01L 33/00; H01L 25/13
(52) U.S. Cl. .......................... 433/29; 362/800; 362/804
(58) Field of Search .................. 433/29, 215; 606/1, 606/13, 16; 607/88; 362/119, 800, 804

(56) References Cited

U.S. PATENT DOCUMENTS

| | | | |
|---|---|---|---|
| 4,149,086 A | 4/1979 | Nath | 250/504 |
| 4,184,196 A | 1/1980 | Moret et al. | 433/29 |
| 4,221,994 A | 9/1980 | Friedman et al. | 315/224 |
| 4,229,658 A | 10/1980 | Gosner | 250/504 |
| 4,281,366 A | 7/1981 | Wurster et al. | 362/32 |
| 4,308,120 A | 12/1981 | Pennewiss et al. | 204/159.23 |
| 4,666,406 A | 5/1987 | Kanca, III | 433/229 |
| 4,698,730 A | 10/1987 | Sakai et al. | 362/311 |
| 4,839,566 A | 6/1989 | Herold et al. | 31/308 |
| 4,935,665 A | 6/1990 | Murata | 313/500 |
| 4,936,776 A | 6/1990 | Kwiatkowski | 433/220 |
| 4,963,798 A | 10/1990 | McDermott | 315/312 |
| 4,989,217 A | 1/1991 | Ostler | 372/107 |
| 5,115,761 A | 5/1992 | Hood | 118/641 |
| 5,123,845 A | 6/1992 | Vassiliadis et al. | 433/215 |
| 5,139,495 A | 8/1992 | Daikuzono | 606/17 |
| 5,151,520 A | 9/1992 | Gottschalk et al. | 548/110 |
| 5,161,879 A | 11/1992 | McDermott | 362/206 |
| 5,214,658 A | 5/1993 | Ostler | 372/23 |
| 5,233,283 A | 8/1993 | Kennedy | 320/13 |
| 5,238,744 A | 8/1993 | Williams et al. | 428/412 |
| 5,275,564 A | 1/1994 | Vassiliadis et al. | 433/226 |
| 5,328,368 A | 7/1994 | Lansing et al. | 433/116 |
| 5,348,552 A | 9/1994 | Nakajima et al. | 606/13 |
| 5,350,834 A | 9/1994 | Bobsein et al. | 528/485 |

(Continued)

FOREIGN PATENT DOCUMENTS

| | | |
|---|---|---|
| DE | 29 27 260 A1 | 2/1980 |
| DE | 25 57 920 B2 | 3/1980 |
| EP | 0 339 841 B1 | 2/1989 |
| EP | 1090607 * | 4/2001 |
| GB | 1 570 507 | 12/1976 |
| WO | WO 99/16136 * | 4/1999 |
| WO | WO 02/33312 * | 4/2002 |

OTHER PUBLICATIONS

Published PCT Patent Application PCT/US99/01126 (WO 99/35995) (Jul. 22, 1999).

(Continued)

Primary Examiner—Ralph A. Lewis
(74) Attorney, Agent, or Firm—Daniel P. McCarthy; Parsons Behle & Latimer

(57) ABSTRACT

A curing light system useful for curing light activated composite materials is disclosed. Various configurations of light emitting semiconductor chips and heat sinks are disclosed, as well as various structures and methods for driving, controlling and using them.

3 Claims, 45 Drawing Sheets

U.S. PATENT DOCUMENTS

| | | | | |
|---|---|---|---|---|
| 5,415,543 | A | 5/1995 | Rozmajzl, Jr. | 433/29 |
| 5,420,758 | A | 5/1995 | Liang | 362/119 |
| D361,382 | S | 8/1995 | Brunsell et al. | 24/177 |
| 5,457,611 | A | 10/1995 | Verderber | 362/32 |
| 5,472,991 | A | 12/1995 | Schmitt et al. | 522/4 |
| 5,485,317 | A | 1/1996 | Perissinotto et al. | 359/712 |
| 5,521,392 | A | 5/1996 | Kennedy et al. | 250/492.1 |
| 5,550,853 | A | 8/1996 | Ostler | 372/34 |
| 5,616,141 | A | 4/1997 | Cipolla | 606/15 |
| 5,634,711 | A | 6/1997 | Kennedy et al. | 362/119 |
| 5,660,461 | A | 8/1997 | Ignatius et al. | 262/241 |
| D385,051 | S | 10/1997 | Wu | D26/2 |
| 5,698,866 | A | 12/1997 | Doiron et al. | 257/99 |
| 5,711,665 | A | 1/1998 | Adam et al. | 433/9 |
| 5,713,738 | A | 2/1998 | Yarborough | 322/215 |
| 5,782,553 | A | 7/1998 | McDermott | 362/245 |
| 5,791,898 | A | 8/1998 | Maissami | 433/164 |
| 5,797,740 | A | 8/1998 | Lundvik | 433/29 |
| 5,803,729 | A | 9/1998 | Tsimerman | 433/29 |
| 5,890,794 | A | 4/1999 | Abtahi et al. | 362/294 |
| 5,908,294 | A | 6/1999 | Schick et al. | 433/29 |
| 5,912,470 | A | 6/1999 | Eibofner et al. | 250/504 H |
| 5,980,295 | A | 11/1999 | Lai et al. | 433/29 |
| 6,008,264 | A | 12/1999 | Ostler et al. | 522/4 |
| 6,019,482 | A | 2/2000 | Everett | 362/184 |
| 6,077,073 | A | 6/2000 | Jacob | 433/29 |
| 6,089,740 | A | 7/2000 | Forehand et al. | 362/573 |
| 6,095,661 | A | 8/2000 | Lebens et al. | 362/184 |
| 6,095,812 | A | 8/2000 | Senn et al. | 433/29 |
| 6,099,520 | A | 8/2000 | Shimoji | 606/2 |
| 6,102,696 | A | 8/2000 | Osterwalder | 433/29 |
| 6,103,203 | A | 8/2000 | Fischer | 422/186 |
| 6,159,005 | A | 12/2000 | Herold et al. | 433/29 |
| 6,200,134 | B1 | 3/2001 | Kovac et al. | 433/29 |
| 6,208,788 | B1 | 3/2001 | Nosov | 385/121 |
| 6,254,388 | B1 | 7/2001 | Yarborough | 433/215 |
| 6,282,013 | B1 | 8/2001 | Ostler et al. | 359/309 |
| 6,318,996 | B1 | 11/2001 | Melikechi et al. | 433/29 |
| 6,322,358 | B1 | 11/2001 | Senn et al. | 433/29 |
| 6,325,623 | B1 | 12/2001 | Melnyk et al. | 433/29 |
| 6,328,456 | B1 | 12/2001 | Mize | 362/311 |
| 6,331,111 | B1 * | 12/2001 | Cao | 433/29 |
| 6,419,483 | B1 * | 7/2002 | Adam et al. | 433/29 |
| 6,439,888 | B1 * | 8/2002 | Boutoussov et al. | 433/215 |
| 6,511,317 | B2 * | 1/2003 | Melikechi et al. | 433/29 |
| 6,611,110 | B1 * | 8/2003 | Fregoso | 315/224 |
| 6,638,063 | B2 * | 10/2003 | Otsuka | 433/29 |
| 6,692,250 | B1 * | 2/2004 | Decaudin et al. | 433/29 |
| 6,692,251 | B1 * | 2/2004 | Logan et al. | 433/29 |
| 6,695,614 | B2 * | 2/2004 | Plank | 433/29 |
| 6,702,576 | B2 * | 3/2004 | Fischer et al. | 433/29 |

OTHER PUBLICATIONS

"3M ESPE Introduces New LED Curing Light" (2 pages) printout from cms.3m.com).

"NGR L.E.D. Curing Light" brochure (4 pages).

"LumaLite Luma 8, LumaArch, LumaCure" (4 pages) (printout from www.luma–lite.com).

"Curing Light XL 3000 " (3 pages) (printout from www.brooks.af.mil).

"LumaCure Cordles Curing Light" (2 pages) (printout from www.brooks.af.mil).

"Compo–T VLC Visible Light Cure Composite Dental Restorative Materials" (4 pages) (Printout from www.yates-motloid.com).

Bayne et al, "Update on dental composite restorations", JADA, vol. 125, Jun. 1994, pp. 687–701.

"Accucure 3000" brochure (2 pages).

"Accucure 1000" brochure (2 pages).

"LaserMed AGD Show Special AccuCure 3000 Laser Show Special" flyer (1 page).

"LumaCure" flyer (1 page).

"ARC Light IIM" brochure (2 pages).

"Introducing the Apolloelight wireless curing light" flyer (1 page).

"Just Cure It" brochure (3 pages) (printed out from www.airtechniques.com).

"Resin Curing Lights: What You Should Know", p. 36 from Contemporary Esthetics and Restorative Practice, Nov., 2001.

"Starlight Starlight p" flyer (1 page).

"Exelite" flyer (1 page).

"Epilar FreeLight" flyer (1 page).

Centrix, Introducing VersaLux the world class battery operated LED curing light that fits in the palm of your hand (Jul.–Aug. 2001) (1 page).

"ZAP Dental Curing" flyer (1 page).

"Exelite" flyer (1 page).

"Elipar Freelight Curing Light" (2 pages) (printout from cms.3m.com).

"Intraoral Resin Curing Lights—Update '96" excerpt from Mar. 1996 CRA newsletter (2 pages).

"All–Cure Standard and Custom Dental Curing Lightguides" (1 page) (Printout from www.all–cure.com).

"Welcome to Bonart Medical Supply" (2 pages) (printout from www.bonartmed.com).

"Bonart" (4 pages listing dental equipment including ART–L1 High Power Light Curing Unit) (printout from www.bonartmed.com).

"Dentamerica—Litex" (2 pages discussing Litex 680A, Litex 682, and Litex 692 curing lights) (Printout from www.dentamerica.com).

"Problems with the Apollo E curing light" (1 page article) (printout from www.imakenews.com).

"Bellini X Ray" (2 pages depicting Sunlite 1275 curing light) (printout from www.bellinixray.com).

"ACTA Curing Light" (2 pages) (printout from www.amadent.com).

"Laser Technology in Dentistry" (3 pages) (printout from dentistry.about.com).

"Synopsis of Visible Light Curing Units" (8 pages summarizing various curing lights) printout from www.brooks.af.mil).

"Zap Dual Curing Light" (2 pages) (printout from www.brooks.af.mil).

"Vivalux II Corlesss Polymerization Unit" (2 pages) (printout from www.brooks.af.mil).

"VersaLux Cordless Curing Light" (2 pages) (printout from www.brooks.af.mil).

"Variable Intensity Polymerizer Light Curing Unit (VIP)" (3 pages) (printout from www.brooks.af.mil).

"Spectrum 800 Curing Unit" (2 pages) (printout from www.brooks.af.mil).

"Optilux 501 Polymerization Unit" (2 pages) (printout from www.brooks.af.mil).

"Optilux 500 Polymerization Unit" (2 pages) (printout from www.brooks.af.mil).

"Optilux 180 & 360 Polymerization Units" (2 pages) (printout from www.brooks.af.mil).

"Hilux 350 Curing Light" (2 pages) (printout from www.brooks.af.mil).

"Epilar Highlight Curing Light" (2 pages) (printout from www.brooks.af.mil).
"Apollo 95E Curing Light" (2 pages) (printout from www-.brooks.af.mil).
"ARC Light II" (2 pages) (printout from www.brooks.af.mil).
"Savings on Curing Lights from Lone Star Dental Corp.", including First Medica Hilux 200, Spring Health Powerlite and Dentamerica Litex (1 page) (printout from www.denteqip.com).
"LED Curing Light" from TOESCO Yoshida Toei Engineering Co., Ltd., (Oct. 2001).
"Dental/Medical Diagnostic Systems, Inc. Receives $4.0 Million Order for Its Wireless Apollo e and Wavelight Curing Unites Based on New LED Technology" (2 pages) (printout from www.compoundsemiconductor.net).
"Heat Data" (2 pages) (regarding rise in tooth pulp temperature with various curing lights).
"Comparison to Other Curing Lights" (2 pages) printout from www.cranews.com).
"Curing Performance" (4 pages) (printout from www.cranews.com).
"Technical Data" (3 pages) (printout from www.cranews.com).
"Photographs" depicting Virtuoso curing light (printout from www.cranews.com).
Caughman, et al., "In Vitro Intrapulpal Temperature Rise with a Variety of Light Sources" (1 page).
Bouschlicher, et al., "Intrapulpal Temperature Increases with LED, QTH and Arc Photoinitiation" (1 page).
Meyer et al., "Decrease in Power Output of Blue LD Curing Lights with Increasing Distance to Filling Surface" (1 page).
Pàrr et al., "Spectral Analysis of Commercial LED Dental Curing Lights" (1 page).
CRA Newsletter, vol. 20, Issue 3, "Intraoral Resin Curing Lights", (Mar. 1996) (2 pages).
CRA Newsletter, "Resin Curing Light, Cordless" (2 pages).
CRA Newsletter, "Visible Curing Lights" (4 pages).
"Power PAC" (3 pages) (printout from www.americandentaltech.com).
"The PAC" (2 pages) (printout from www.americandentaltech.com).
"The Science of Curing" (8 pages) (printout from www.lasermed.com).
"The Accucure 1000" (2 pages) (printout from www.lasermed.com).
"The Accucure 3000" (2 pages) (printout from www.lasermed.com).
"RemeCure CL15" (1 page) (printout from www.remedent.com).
Guido Coracci, Giovanni Mori, Luca Casa de Martinis, "Curing light intensity and marginal leakage of resin composite restorations", Quintessence International, vol. 27, No. 5/1995 (8 pages).
Hiromass Kato, "Relationship between the velocity of polymerization and adaptation to dental cavity wall of light cured composites", Dental materials journal 6(1):32–37 (1987) (6 pages).
Uno, S., Asmussen, E., "Selected variables in bonding to dentin", Scand. J. Dent. Res. 1992: 100: 130–2 (2 pages).
G.L. Unterbrink and R. Muessner, "Influence of light intentisty on two restorative systems", J. Dent., vol. 23, No. 3, pp. 183–189 (1995) (7 pages).

Email from Jens Jenkins [Jjenkins@wnspat.com] to Dan McCarthy Re: Pending Application Information dated Wednesday, Apr. 3, 2002 (2 pages) and listing 5 pending U.S. patent applications.
A. Mehl, H. Staunau, D. Schreyger, K.H. Kunzelmann, R. Hickel, LMU University Dental School, D–80336 Munich Germany, 1 page abstract, Journal of Dental Research, vol. 74, 1995, special issue p. 462.
Sakaguchi and Berge, "Light Intensity Effects on Degree of Cure Posterior Composite", #1972, IADR 1997 (4 pages).
Shigero Uno and Erik Asmussen, "Marginal Adaptation of A Restorative Resin Polymerized At A Reduced Rate" (5 pages).
Peter Koran & Ralf Kurschner, Effect of sequential versus continuous irradiation of a light cured resin composite on shrinkage, viscosity, adhesion, and degree of polymerization, CE Article #3–198, Americal Journal of Dentistry, vol. 11, No. 1, Feb. 1998 (6 pages).
A. Mehl, R. Hickel, K.H. Kunzelmann, Dental School Munich Germany, "Physical properties and gap formation of light cured composites with and without softstart–polymerization" faxed copy dated May 30, 1996 (27 pages).
K.J. Reinhardt and J. Vahl, "Uncertainties in the Testing of Photopolymers" 11 pages.
A.J. Fellzer, L.H. Dooren, A.J. De Gee, and C.L. Davidson, "Influence of light intensity on polymerization shrinkage and integrity of restoration cavity interface", Eur. J. Oral Sci. 1995; 103: 322–326 (5 pages).
A. Mehl, M. Sobota, R. Hickel, "Soft start polymerization of composites in class V cavities" (10 pages).
Saliha S. Davidson–Kaban, Carel L. Davidson, Albert J. Feilzer, Anton J. de Gee, Nejdet Erdilek, "The effect of curing light variations on bulk curing and wall to wall quality of two types and various shades of resin composites", Dent Mater 12:344–352, Nov. 1997 (9 pages).
Letter from John Vickers, III, General Counsel to American Dental Technologies, to Daniel McCarthy dated May 2, 2000.
Letter from Dr. Roland Brem of ESPE Dental AG to Daniel McCarthy dated May 11, 2000.
Letter from Dr. Roland Brem of ESPE Dental AG to Daniel McCarthy dated May 31, 2000.
Letter from Dr. Roland Brem of ESPE Dental AG to Daniel McCarthy dated Jun. 8, 2000.
Facsimile dated Friday, May 29, 1998 from Dr. Frederick M. Parkins of the School of Dentistry, University of Louisville to Bob Dalton of ADT regarding final draft sent to Tony Angelini (6 pages).
Dental Cadmos 7/93, pp. 62–63.
A. Mehl, M. Sobota, R. Hickel, "Softstartpolymerisation von Kompositen in Klasse V Kavitaten", Dtsch Zahnarzti Z 52 (1997) in German (4 pages).
G. Goracci, L. Casa de Martinis, G. Mori, "Compositi e Polymerizzazione Lenta", Dental Dadmos 13/92 in Italian (12 pages).
G. Goracci, L. Casa de Martinis, G. Mori, "Polymerizzazione di Materiali Compositi", Dental Dadmos 7/93 in Italian (14 pages).
J. Reinhardt and J. Vahl Munster, "Unsicherheiten bei der Prufung von Photopolymerisaten", Dtsch zahnarztl Z. 36, 635–640 (1981) in German.
10 Mississippi and you're done! New NRG LED Curing Light brochure from Dentsply Caulk (4 pages).
Exelite advertisement from Toesco.(1 page).

Epilar Freelight advertisement from ESPE (1 page).

Centrix The Catalog for the Dental Professional showing Versalux LED curing light (1 page).

Introducing the Apolloe e light wireless curing light advertisement for LED curing light from DMD (1 page).

LumaCure New Technology World's first patented solid state dental Curing Light (1 page).

Starlight and Starlight p by Mectron Medical Technology (1 page).

ZAP Dual Curing—A curing light that can Fast Cure with Soft Cure results? From Soft Core Texas, Inc. (1 page).

Polymerisation im Schongang Epilar Highlight from ESPE (6 pages).

Dentistry Today, Jan. 1998, front page and page 70 showing Kreativ Inc. Kerativ Kuring Light (2 pages total).

Dental Products Report, Oct. 1997, front page and page showing ESPE Pentamix and Epilar Highlight (2 pages total).

Dental Products Report, Nov. 1997, front page and page showing Kreativ Microdentistry System (2 pages total).

* cited by examiner

CURING LIGHT

CROSS-REFERENCE TO RELATED APPLICATIONS

This patent application is a continuation-in-part of Ser. Nos. 10/016,992; 10/017,272, now U.S. Pat. No. 6,783,362; 10/017,454; and 10/017,455; each of which was filed on Dec. 13, 2001, and each of which is a continuation-in-pad of U.S. patent application Ser. No. 09/405,373 filed on Sep. 24, 1999, now U.S. Pat. No. 6,331,111, and priority is claimed thereto. Priority is also claimed to U.S. Provisional Patent Application Ser. No. 60/304,324 filed on Jul. 10, 2001.

BACKGROUND OF THE INVENTION

The inventions relate to the field of curing lights that may be used to cure light activated composite materials. More particularly, the inventions relate to curing lights of various configurations that use semiconductor light sources to provide light of a wavelength and power level desired to effect curing. In many fields, composite materials, such as monomers and an initiator, are cured into durable polymers by use of a light source of appropriate wavelength to excite the initiator into initiating polymerization, and sufficient power to carry polymerization through to adequate completion.

In the prior art, various light sources have been used for the purpose of curing composite materials. Halogen bulbs, fluorescent bulbs, xenon bulbs, and plasma-arc lights have been used. More recently, there have been some efforts to produce an effective curing light using light emitting diodes (LED's), but those efforts have not met with widespread acceptance in the marketplace.

The prior art described above suffers from several disadvantages. First, many of those prior art lights generate a wide spectrum of light rather than light just of the desired wavelength for composite curing. Consequently, those prior art lights generate unnecessary heat. Second, many of those prior art lights require light transfer systems such as a light guide or fiber, which many embodiments of the present invention omit, providing a smaller and more efficient unit. Third, many of the prior art systems require an elaborate cooling system to handle heat, creating a large, heavy and expensive curing light. Many embodiments of the invention use a unique heat sink structure that avoids the need for complicated, noisy and expensive cooling systems. Many embodiments of the invention use a semiconductor light source and package which provides high power light for use in curing composite materials. Additional points of difference between the inventions and the prior art will become apparent upon reading the text below in conjunction with the appended drawings.

SUMMARY OF INVENTION

It is an object of some embodiments of the invention to provide a curing light system that uses a semiconductor light source to produce light capable of curing composite materials. Curing composite materials will involve polymerizing monomers into durable polymers. Various physical, electrical and semiconductor structures, materials and methods are provided to achieve this object. Additional objects, features and advantages of the invention will become apparent to those skilled in the art upon reading the specification and reviewing the appended drawings.

BRIEF DESCRIPTION OF THE DRAWINGS

FIG. 16b depicts a cross section of the light of FIG. 16a.

FIG. 22d depicts a perspective view of the chip package of FIG. 22a.

FIG. 25b depicts a perspective view of the array of surface-mounted chips of FIG. 25a.

FIG. 26b depicts a perspective view of the array of surface-mounted chips of FIG. 26a.

FIG. 27b depicts a perspective view of the array of surface-mounted chips of FIG. 27a.

FIG. 28b depicts a perspective view of the array of surface-mounted chips of FIG. 28a.

FIG. 31b depicts a bottom view of the device of FIG. 31a.

FIG. 32b depicts a bottom view of the device of FIG. 32a.

FIG. 33b depicts a bottom view of the device of FIG. 33a.

DETAILED DESCRIPTION

The inventions include various embodiments of curing light systems useful for curing light activated composite materials, principally by polymerizing monomers into durable polymers. The invented curing light systems have application in a variety of fields, including but not limited to medicine and dentistry where composite materials with a photoinitiator are used. The photoinitiator absorbs light of a particular wavelength and causes polymerization of the monomers into polymers.

Composite materials are applied to a surface and later cured by a variety of methods. One method includes use of a photoinitiator or multiple photoinitiators in the composite material. After the composite material has been placed in a desired location, light of a wavelength that activates the photoinitiator is applied to the composite. The light activates the photoinitiator and initiates curing of the composite material. In order to effect complete curing, the light must be of a wavelength to which the photoinitiator is sensitive, the light must be of a power level that will cause curing, and the light must be applied to the composite material for a sufficient duration of time. Although the light used to activate the photoinitiator must be of a wavelength to which a photoinitiator is sensitive, the light can come from a variety of sources, including gas lasers solid state lasers, laser diodes, light emitting diodes, plasma-arc lights, xenon-arc lights, and conventional lamps. In the present inventions, light is produced from a variety of different semiconductor chips arranged in numerous configurations.

Figure 1:
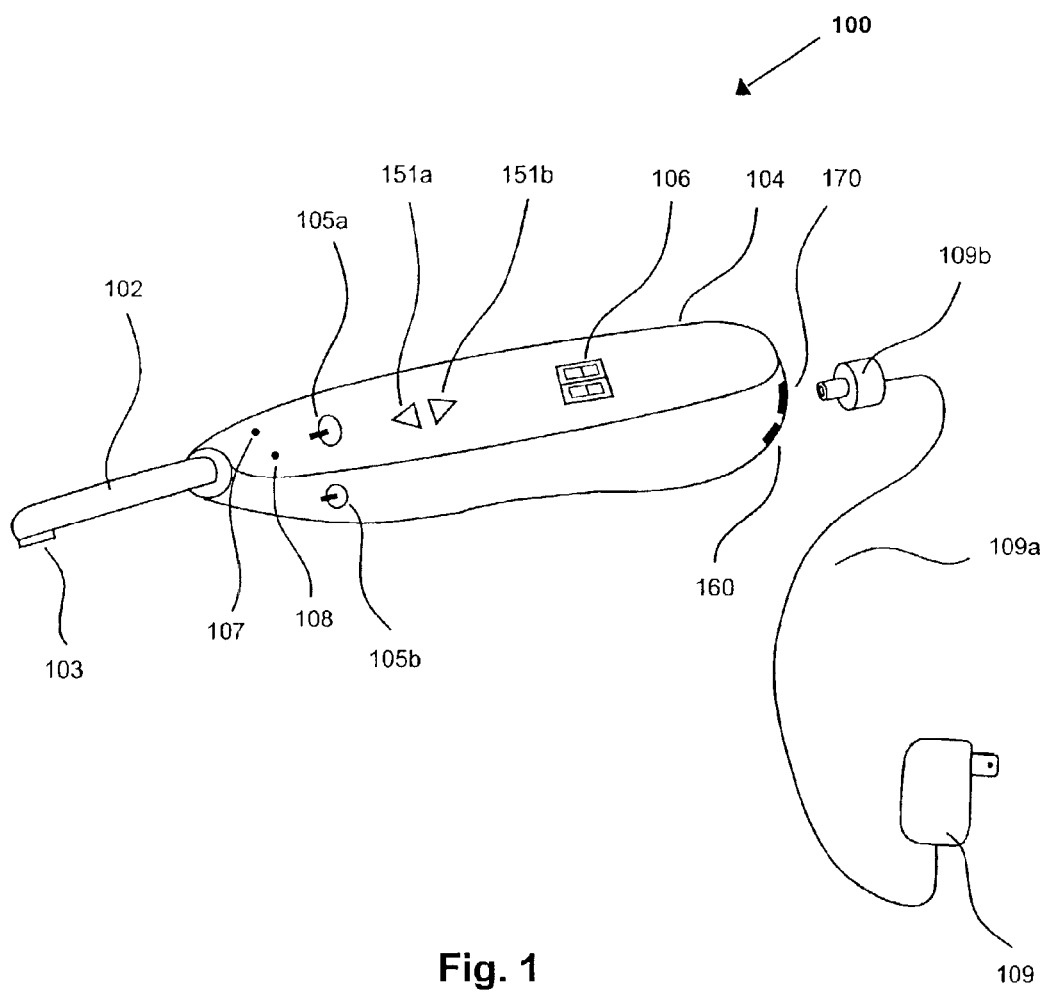
FIG. 1 depicts a battery-powered Curing light that uses a single light emitting diode chip as a light source.
Figure 2:
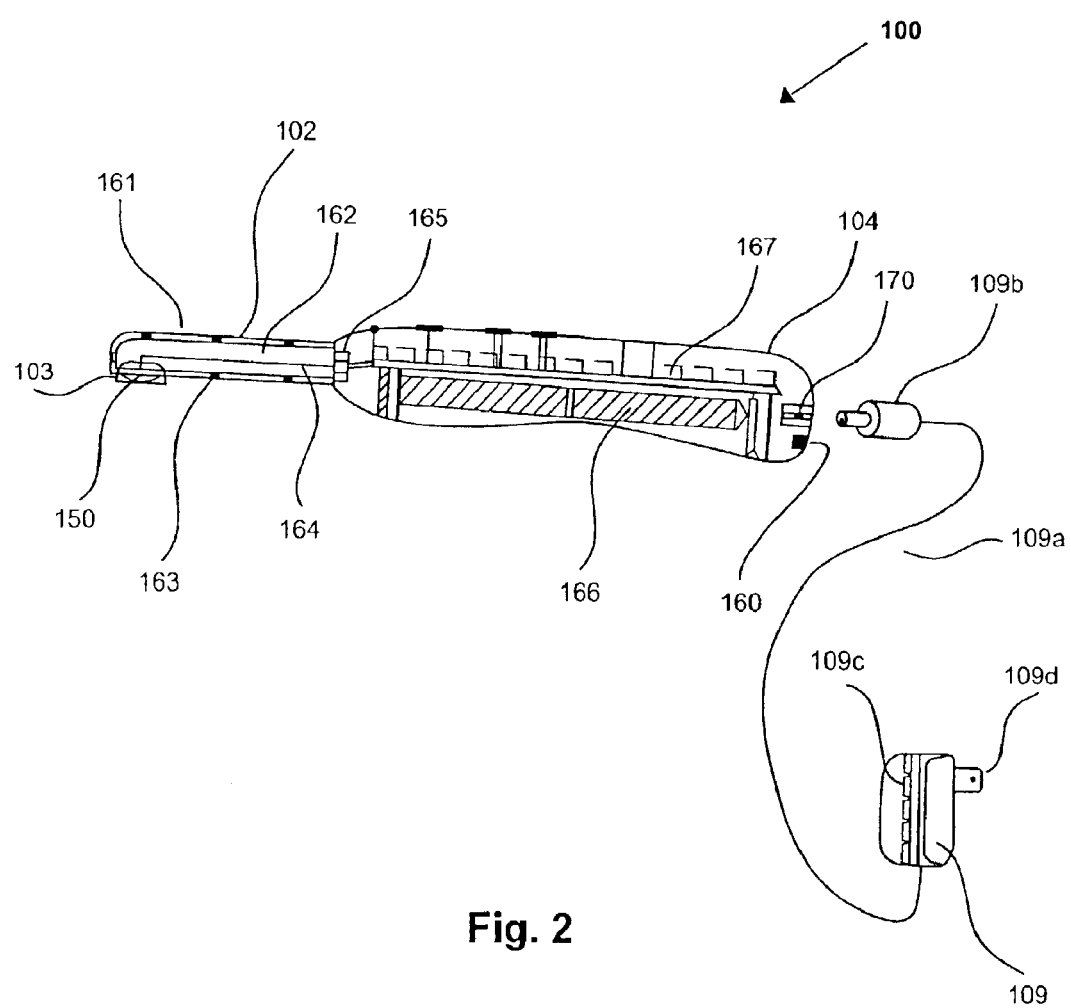
FIG. 2 depicts a cross-section of the light of FIG. 1.

FIG. 1 depicts a battery-powered curing light 100 that uses a single light emitting diode chip as a light source. FIG. 2 depicts a cross-section of the light 100 of FIG. 1. The portable curing light system 100 includes a light source module 102 which generates light of a desired wavelength or multiple wavelengths for activating a photoinitiator or multiple photoinitiators and initiating curing of a light activated composite material. The light source module 102 has a light shield 103 for blocking light generated by the light emitting semiconductor chip(s) 150 from reaching human eyes and skin. The apparatus 103 could also be configured as a lens or focusing cone for modifying the footprint of light emitted by the curing light. The light emitting semiconductor chip(s) 150 are located at the distal end of the curing light, and at the distal end of the light source module 102. The chip(s) 150 are oriented to emit light at generally a right angle with the longitudinal axis of the light source module or the longitudinal axis of the curing light handpiece, although chips could be mounted to emit light at from about a 45 degree angle to about a 135 degree angle with the longitudinal axis of the light source module, heat sink, or handpiece as desired. The curing light system 100 includes a housing 104 for containing and protecting electronic circuits and a DC battery pack. In some embodiments, the light emitting semiconductor chip(s) may be powered by from less than about 25 milliamps to more than about 2 amps. Many embodiments of the inventions will have chip(s) powered from about 350 milliamps to about 1.2 amps of current. Higher power embodiments of the inventions will often use more than about 100 milliamps of current.

A switch 105a is provided on the top of the housing 104 facing a direction opposite from the direction that light would be emitted from the light source module 103. A second switch 105b is provided on the side of the housing. The switches 105a and 105b are devices such as a button or trigger for turning the light emission of the curing light on and off. A timer 106 is provided to control the duration of time that the curing light emits a beam of light. Control buttons to set and adjust the timer are depicted as 151a and 151b.

An audible indicator or beeper may be provided in some embodiments of the invention to indicate when light emission from the curing light begins and ends. A first light emitting diode indicator lamp 107 is located on the housing in a visible location in order to indicate to the user low battery power. A second light emitting diode indicator lamp 108 is located on the housing in a visible location in order to indicate to the user that the battery is being charged. A main on/off switch to the curing light 160 is provided at the rear or proximal end of the housing. A wavelength selector may be provided in some embodiments of the invention so that the user may select the wavelength of light that he wishes to emit from the curing light, depending on the wavelength sensitivity of the photoinitiator in the composite material that he is using. The user may also select a combination of two or more wavelengths of light to be emitted together in some embodiments of the invention.

A separate battery charger module 109 is included in order to receive AC power from a traditional wall socket and provide DC power to the curing light system for both charging the batteries and powering the light source and control circuitry when the batteries if desired. The battery charger module 109 has a cable 109a and a plug 109b for plugging into a receptacle or connector 170 on the proximal end of the curing light housing 104. The battery charger module 109 includes circuitry 109c for controlling battery charging of batteries 166.

The light module 102 has a casing 161 that encases an elongate heat sink 162. The casing 161 is separated from the heat sink 162 by a buffer layer 163 such as insulation tape and an air space may be provided therebetween for heat dissipation. Electrically conductive wires 164 to power the light-emitting semiconductor chip(s) 150. Internally, we can see that the heat sink 162 is an elongate and curved structure which positions a semiconductor chip at its end in a convenient place for use without a light guide. At the distal end of the heat sink 162, there may be a smaller primary heat sink or semiconductor chip module which includes a smaller primary heat sink. A semiconductor module may be covered by a protective cover or dome or a focus lens. The heat sink 162 may be an elongate structure or other shape as desired. Use of an elongate heat sink 162 rapidly transfer heat away from the chip(s) 150 for heat dissipation. If heat transfer and dissipation are not handled adequately, damage to the chip(s) 150 may result, or light output of the chip(2) 150 may be diminished.

The light source module 102 is removable from the housing 104 and interfaces therewith and mounts thereto by a connection plug 165. One or more batteries 166 are provided to power the curing light during use. The curing light may have control circuitry 167 located in the housing 102. Battery charger 109c is located in the power supply 109 for controlling battery recharging and direct powering of the curing light from wall outlet power when the batteries are low. The power supply 109 has an AC plug 109d.

A unique advantage of the curing light system depicted in several embodiments of the invention is that all components, including the light source, batteries, control circuitry and user interface are conveniently located in or on a handpiece. This results in a very portable, yet compact and easy to use curing light system. Only when the batteries are being charged would the user need to have a cord attached to the curing light system or even be in the vicinity of AC power. However, the light system can be operated using power from a battery charger when the battery pack is being charged or when no batteries are being used.

Figure 3:
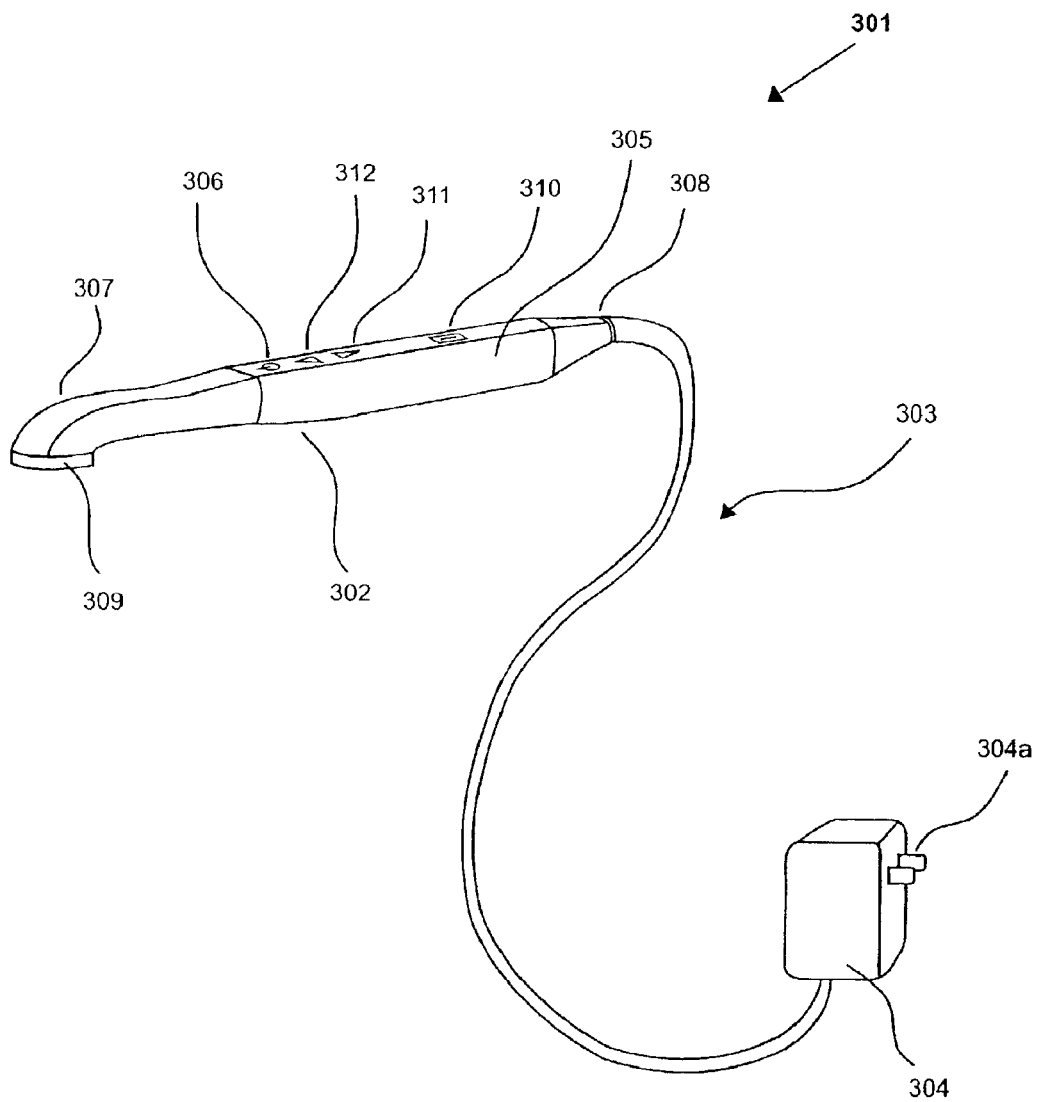
FIG. 3 depicts an AC-powered Curing light that uses a single light emitting diode chip as a light source.
Figure 4:
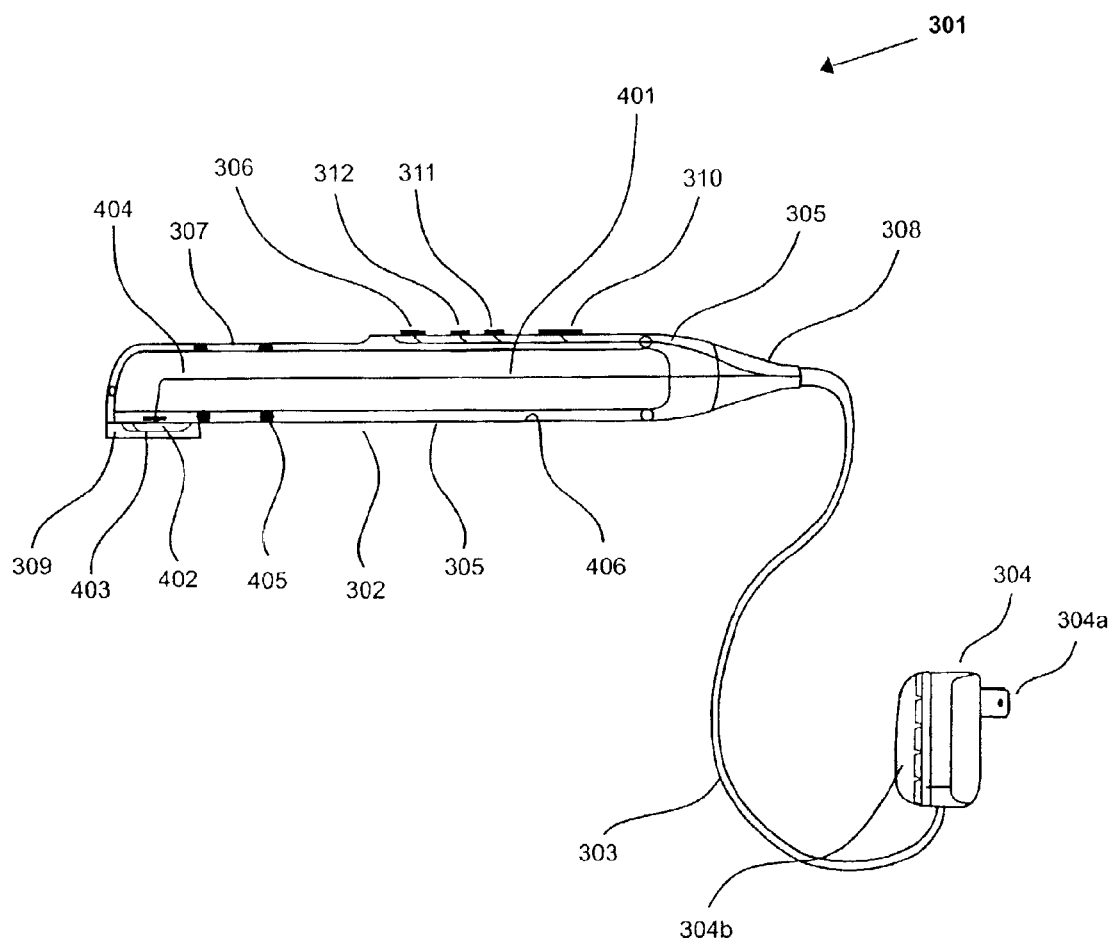
FIG. 4 depicts a cross section of the light of FIG. 3.

FIG. 3 depicts an AC-powered curing light that uses a single light emitting diode chip as a light source. FIG. 4 depicts a cross section of the light of FIG. 3. Referring to these figures, one embodiment of a curing light system 301 of the invention is depicted. The curing light system 301 includes a handpiece or wand 302, cabling 303, and a power supply 304 with an AC plug 304a. Curing light control circuitry 304b may be located within the power supply 304 and is remote from the wand 302 in order to keep the wand compact and light weight. The handpiece or wand 302 has minimum size, weight and componentry for convenience of use. The handpiece 302 includes a housing 305, an on/off switch or light output control 306, an integral light source module 307, and a device 309 which may be a light shield, light reflective cone or focus lens. The handpiece 302 receives electrical power from cabling 303. A cable strain relief device 308 may be provided. A timer 310 may be provided with timer adjustment buttons 311 and 312 in order to control timed duration of light output from the curing light. All control circuitry 304b is located in a module remote from the handpiece 302.

Referring to the cross section of FIG. 4, it can be seen that the heat sink 401 may be configured as an elongate device with a planar mounting platform on its distal end for mounting chips or chip modules thereto. The heat sink has a longitudinal axis, and the light emitting semiconductor chip(s) may be oriented at an angle with the longitudinal axis of the heat sink from about 45 to about 135 degrees. In some embodiments of the invention, the chips will be oriented to emit light at an angle with the heat sink longitudinal axis of 70 to 110 degrees, 80 to 100 degrees, or about 90 degrees. The heat sink distal end may be curved as desired to position a light emitting semiconductor device 401 thereon to be positioned in a location for convenient use. The semiconductor device 402 may be covered with a protective window, dome or focus lens 403. The heat sink may occupy less than 50% of the length of the wand, more than 50% of the length of the wand, 60% of the length of the wand, 70% of the length of the wand, 80% of the length of the wand, 90% of the length of the wand, or up to 100% of the length of the wand. Electrical wire 404 provides power to the light emitting semiconductor device 402. Insulation means 405 such as rubber insulators or insulation tape separate the heat sink 401 from the casing 305 and provide for airspace 406 therebetween for ventilation and heat dissipation.

Figure 5:
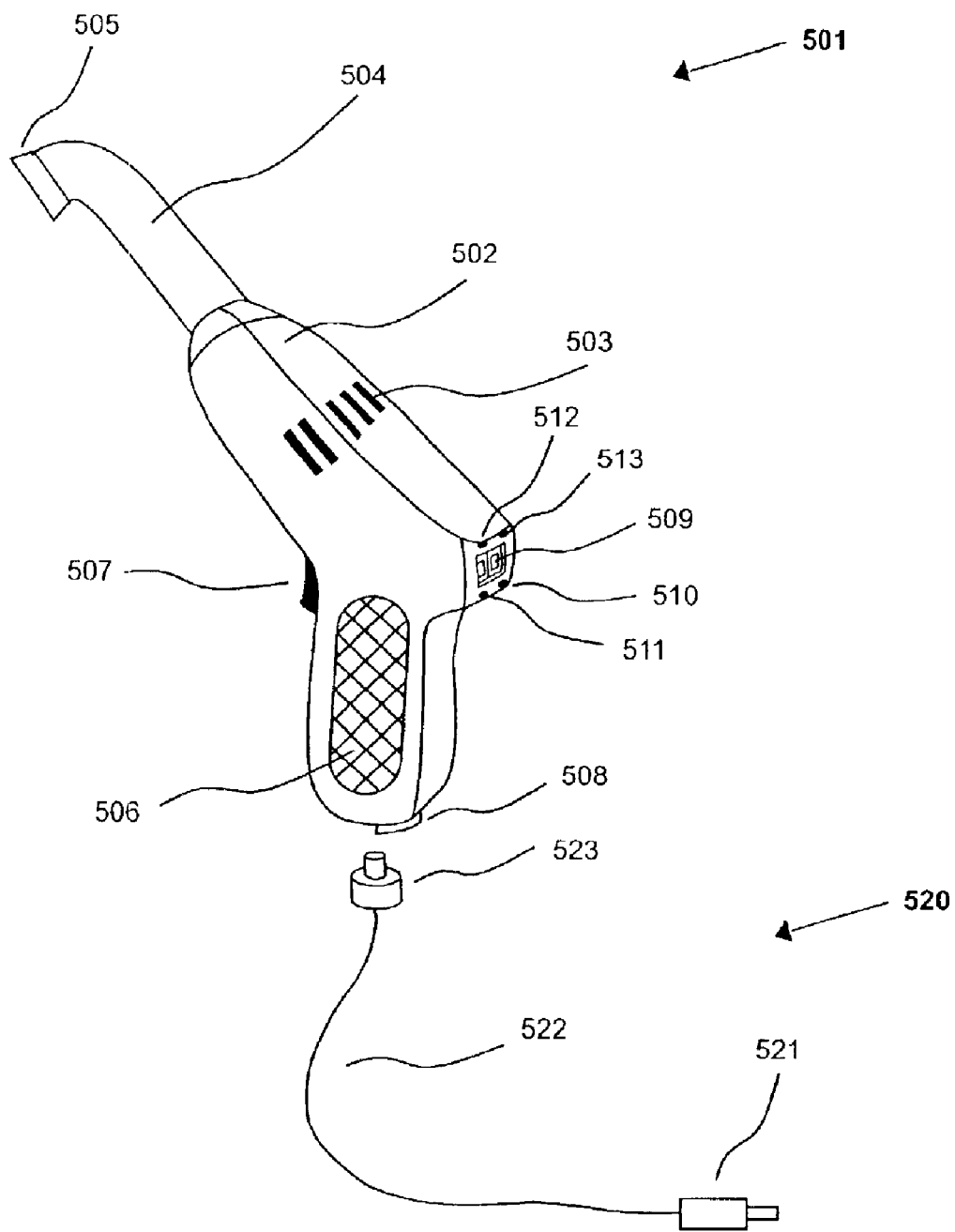
FIG. 5 depicts a battery-powered curing light that uses two light emitting diode chips as a light source.
Figure 6:
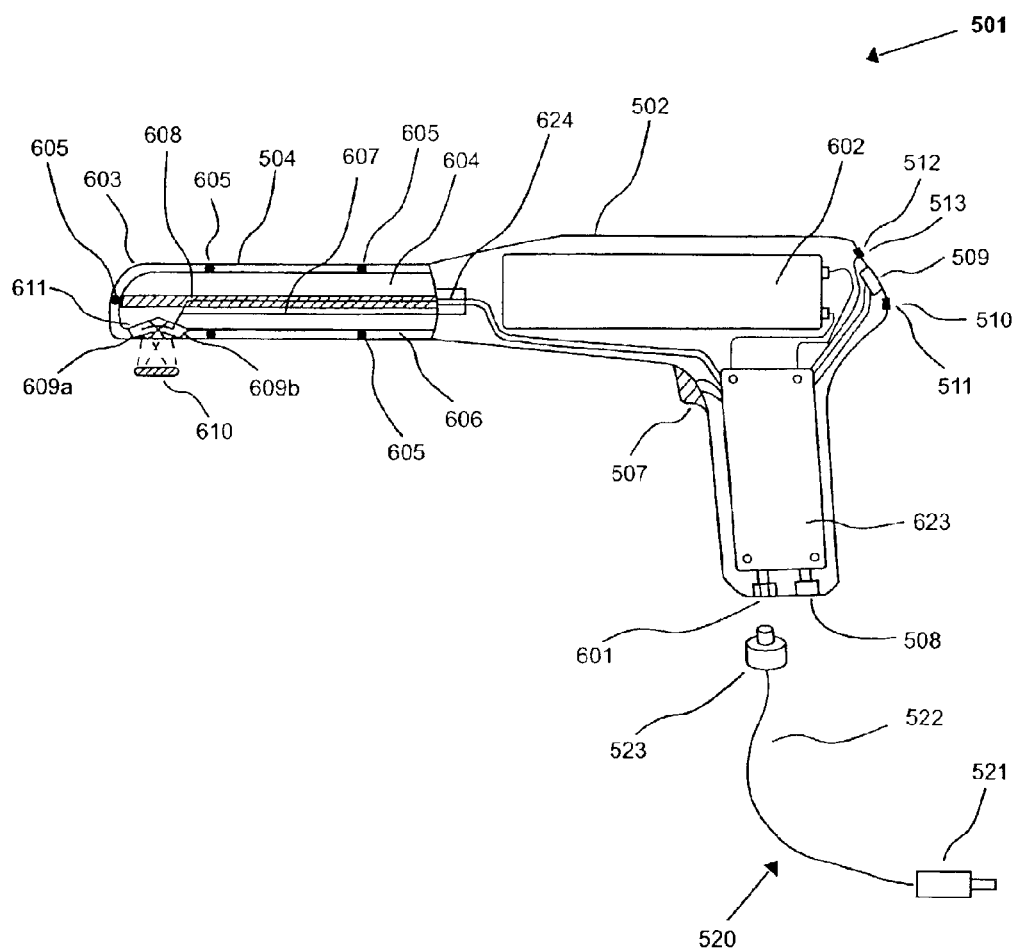
FIG. 6 depicts a cross-section of the light of FIG. 5.

FIG. 5 depicts a battery-powered curing light 501 that uses two light emitting diode chips as a light source. FIG. 6 depicts a cross-section of the light 501 of FIG. 5. The curing light 501 includes a housing or casing 502 for containing and protecting the curing light components. A series of vents 503 are provided in the housing 502 to permit heat to escape therefrom and to permit air circulation therein. At the distal end of the housing 502, a light module 504 is provided. The light module 504 may include an angled tip and may be removable and replaceable with other light modules of differing characteristics as desired. A light shield, light reflective cone or focus lens 505 is provided at the distal end of the light module 504. At the proximal end of the curing light 501, a handle 506 is provided for grasping the curing light. An on-off switch or trigger 507 is provided on the distal side of the curing light handle 506 for effecting light emission. On the proximal side of the curing light handle 506, a main switch 507 for powering up the curing light 501 is located. A timer 509 with timer adjustment buttons 510 and 511 is provided to time the duration of light output. Indicator lights 512 and 513 are provided to indicate low battery and battery charging. A battery charger module 520 is provided with a power supply 521, cable 522 and plug 523. The plug fits into receptacle 601 for charging the battery 602 of the curing light 501.

Referring to FIG. 6, Light module 504 includes a casing 603 that contains an elongate heat sink 604 that is separated from the casing 603 by insulators 605 to form a ventilating and heat-dissipating air space 606 therebetween. Heat sink 604 may include a thermoelectric cooler material 608 thereon for enhanced heat dissipation. Electrical wires 607 power a pair of light emitting semiconductor devices or modules 609a and 609b. The semiconductor devices 609a and 609b are mounted on the heat sink 604 at a mounting receptacle 611 that has two adjacent angled planes oriented to cause the light output beams from the semiconductor devices 609a and 609b to overlap to provide an overlapped and enhanced intensity light footprint 610. The mounting planes are oriented at an angle of from about 10 to about 180 degrees with respect to each other. The curing light 501 also includes a timer 509 with timer control buttons 621 and 622, and electronic control circuitry 623. A battery pack 602 is located inside casing 502 to provide operating power. The light module 504 is connected to housing 502 using an electrical plug 624. The light module 504 can therefore be unplugged and replaced with another light module of different power characteristics or which emits a different wavelength of light for different usage applications.

Figure 7:
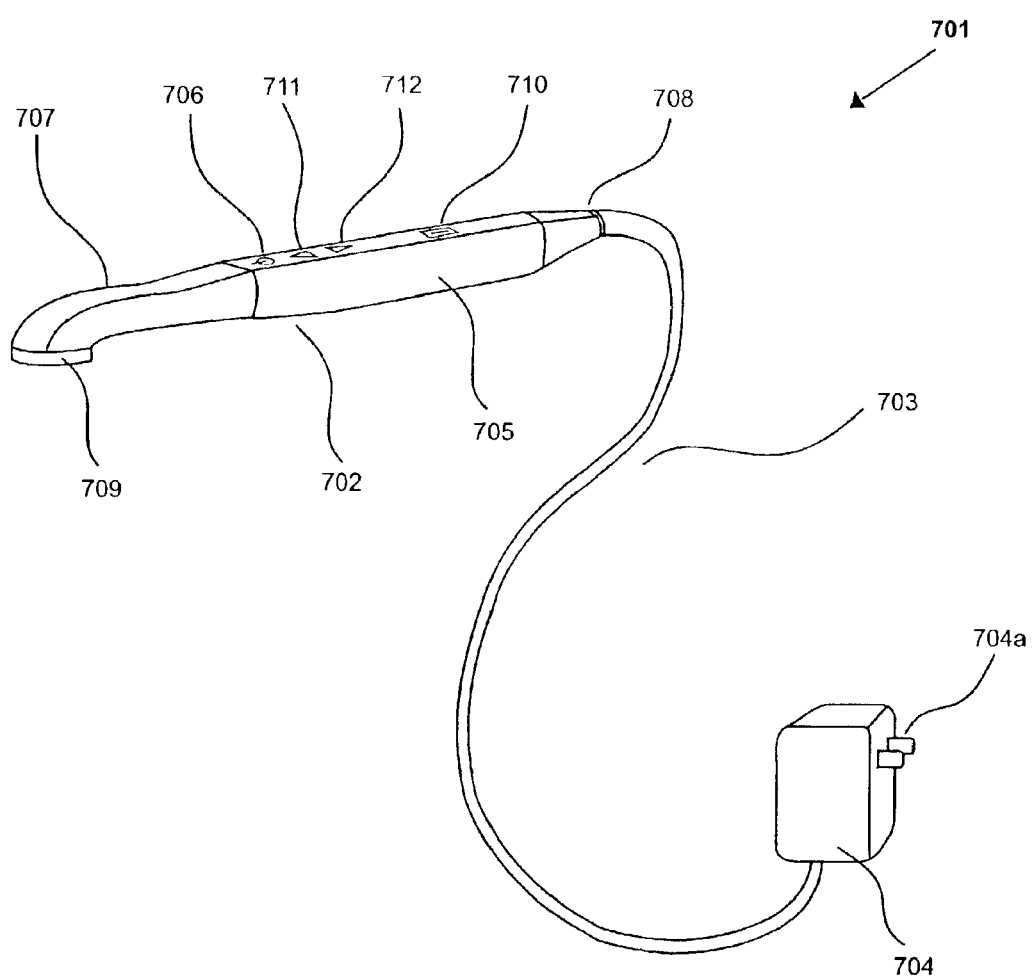
FIG. 7 depicts an AC-powered curing light that uses two light emitting diode chips as a light source.
Figure 8:
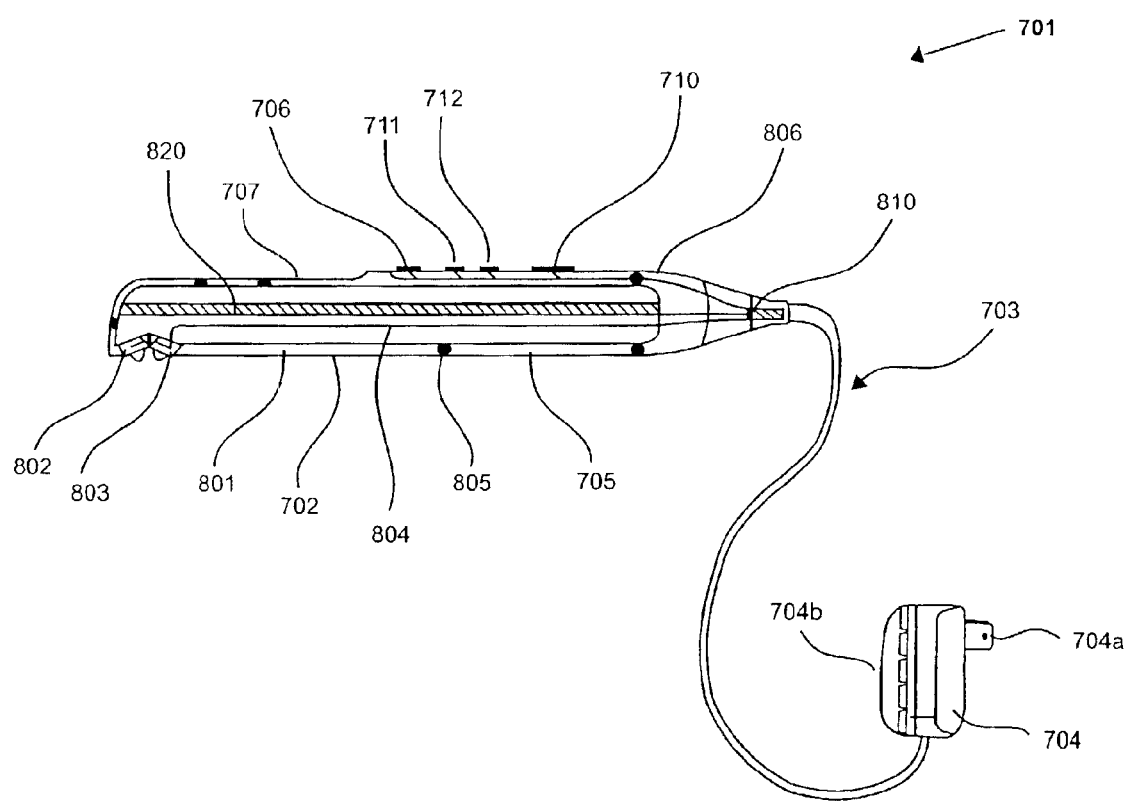
FIG. 8 depicts a cross-section of the light of FIG. 7.

FIG. 7 depicts an AC-powered curing light 701 that uses two light emitting diode chips as a light source. FIG. 8 depicts a cross-section of the light 701 of FIG. 7. The curing light system 701 includes a handpiece or wand 702, cabling 703, and a power supply 704 with an AC plug 704a. Control circuitry 704b is located within the power supply 704 and is remote from the wand 702 in order to keep the wand compact and light weight. The handpiece or wand 702 has minimum size, weight and componentry for convenience of use. The handpiece 702 includes a housing 705, an on/off switch or light output control 706, an integral light source module 707, and a light shield 709. The handpiece 702 receives electrical power from cabling 703. A cable strain relief device 708 may be provided. A timer 710 may be provided with timer adjustment buttons 711 and 712 in order to control timed duration of light output from the curing light. All control circuitry 704b is located in a module remote from the handpiece 702. Referring to the cross section of FIG. 8, it can be seen that the heat sink 801 may be configured as an elongate device with a longitudinal axis shared with the longitudinal axis of the wand. The light emitting semiconductor chip 802 and 803 are mounted to the heat sink 801 at an acute angle to each other in order to produce an overlapping and enhanced intensity light footprint. The heat sink distal end may be curved as desired to position the light emitting semiconductor devices thereon for convenient use. The semiconductor devices 803 and 803 may be covered by a protective window, dome or focus lens. The heat sink may occupy less than 50% of the length of the wand, more than 50% of the length of the wand, 60% of the length of the wand, 70% of the length of the wand, 80% of the length of the wand, 90% of the length of the wand, or up to 100% of the length of the wand. Electrical wire 804 provides power to the light emitting semiconductor devices 802 and 803. Insulation means 805 such as rubber insulators or insulation tape separate the heat sink 801 from the casing 705 and provide for airspace 806 therebetween for ventilation and heat dissipation. A connection plug 810 is provided for connecting the power module to the curing light. Thermoelectric cooler material 820 is optionally provided on the heat sink for enhanced cooling.

Figure 9:
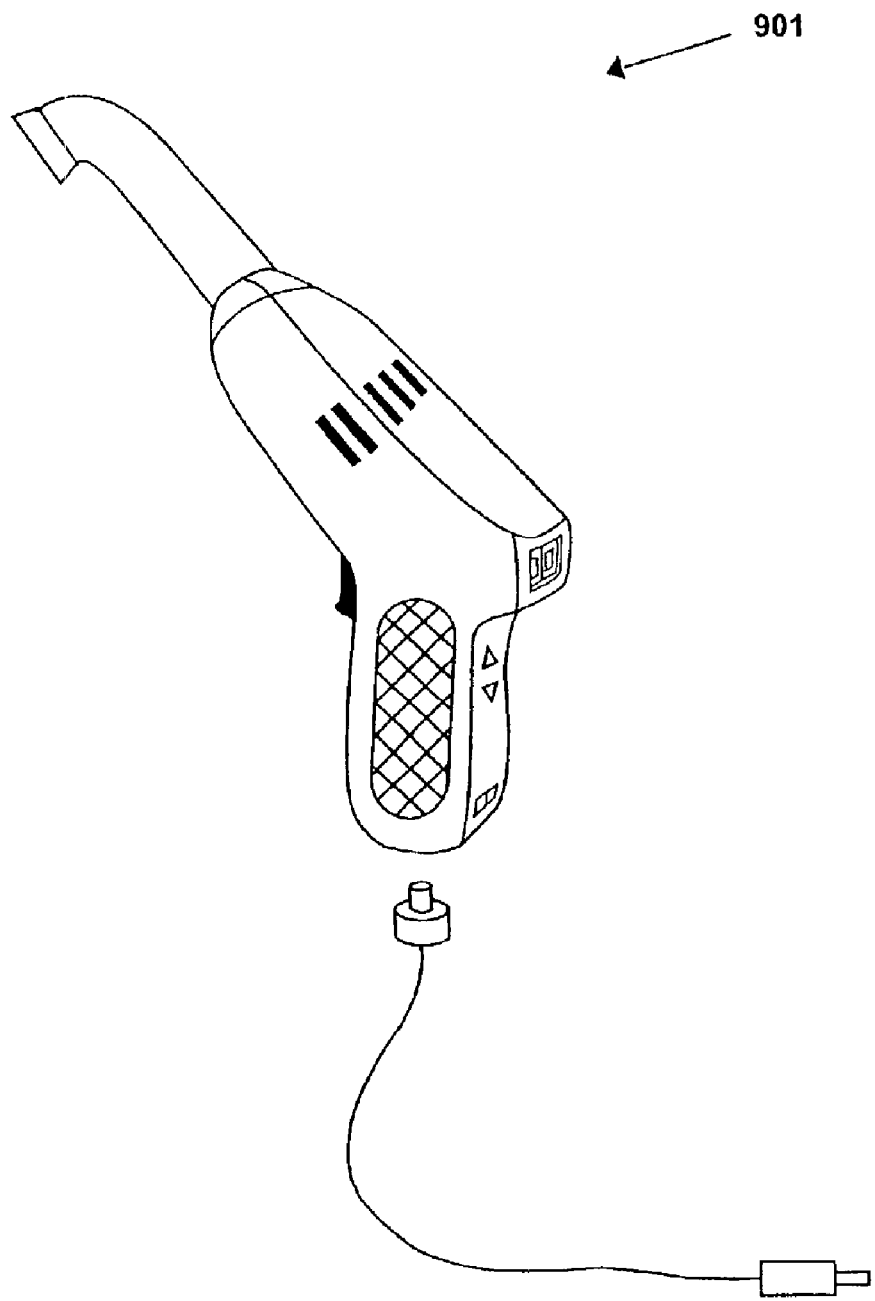
FIG. 9 depicts a battery-powered curing light that uses three light emitting diode chips as a light source.
Figure 10:
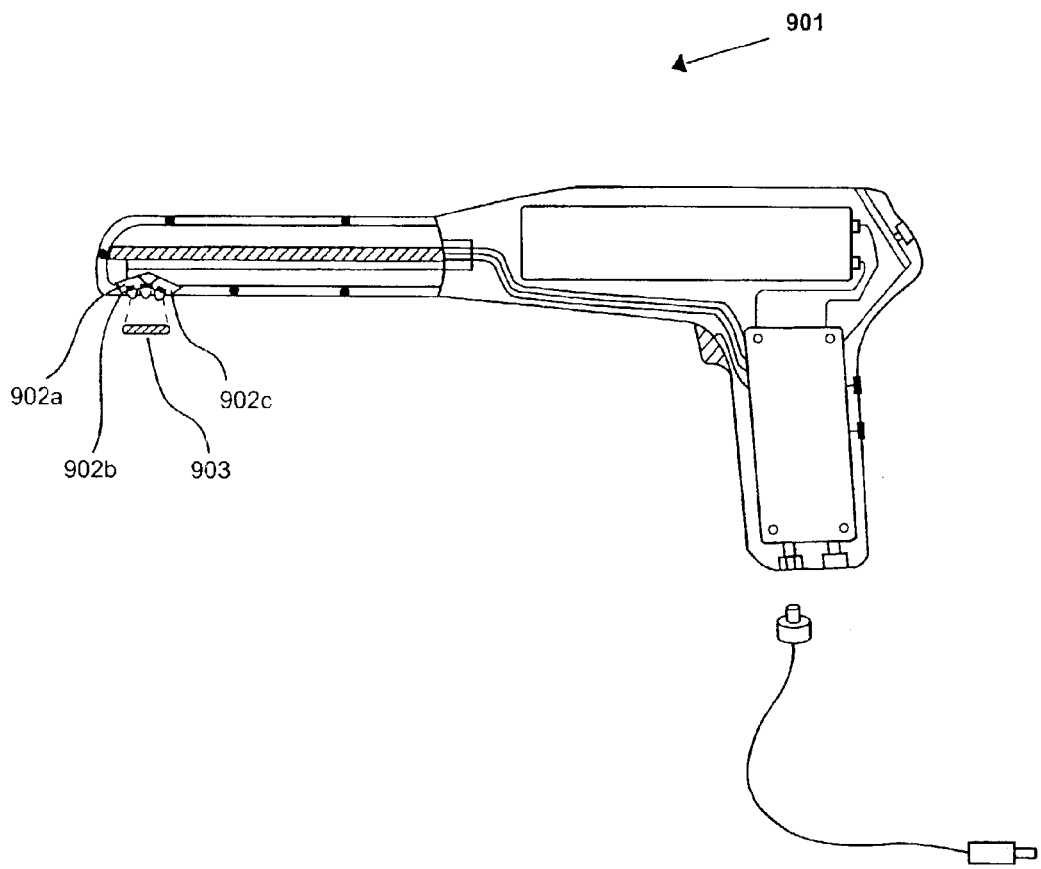
FIG. 10 depicts a cross-section of the light of FIG. 9.

FIG. 9 depicts a battery-powered curing light 901 that uses three light emitting diode chips or modules as a light source. FIG. 10 depicts a cross-section of the light 901 of FIG. 9. The componentry of this curing light is as generally described previously except for its three light emitting diode light source structure. It uses three light emitting diode chips or chip modules 902a, 902b and 902c arranged in complementary angled configuration so that the light beams emitted by each overlap at a desired distance from the light source to form an overlapped and enhanced intensity light footprint 903. The arrangement of 3 LED's is described elsewhere in this document.

Figure 11:
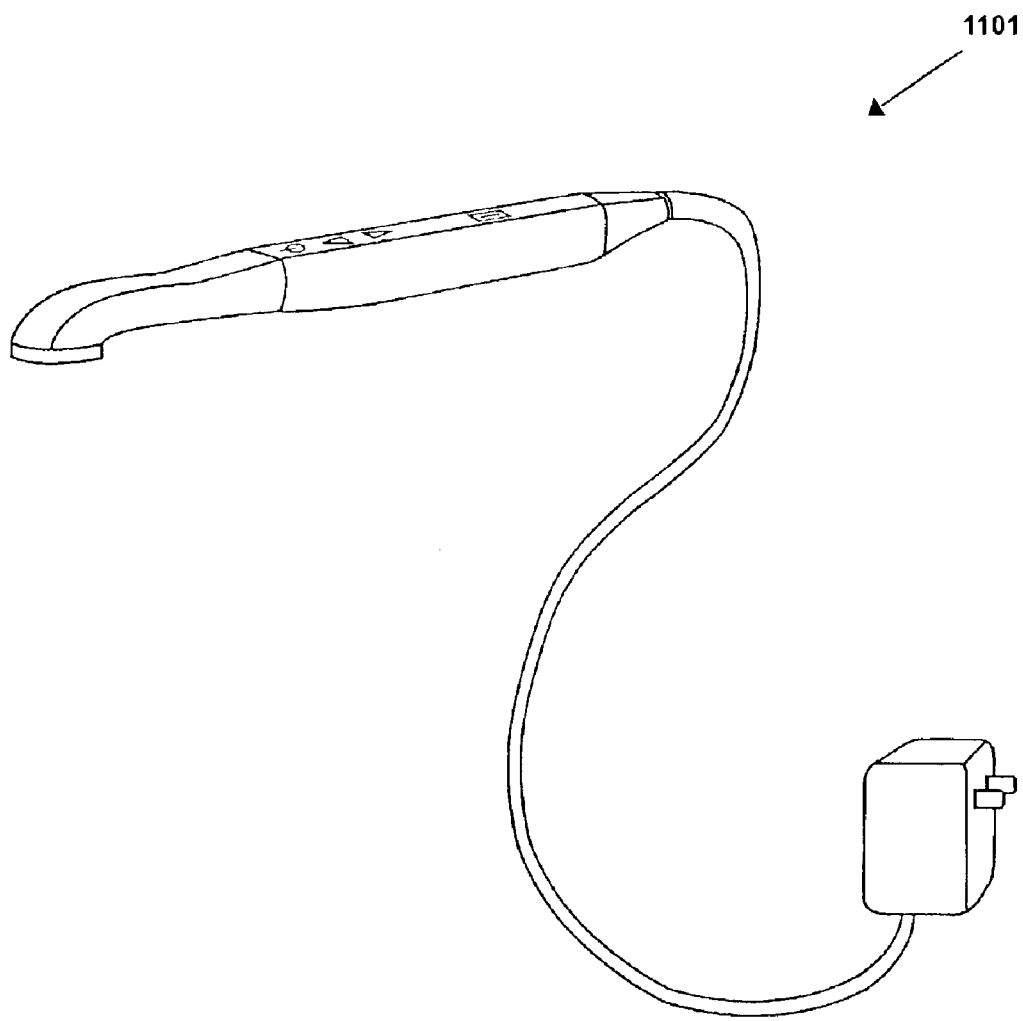
FIG. 11 depicts an AC-powered curing light that uses three light emitting diode chips as a light source.
Figure 12:
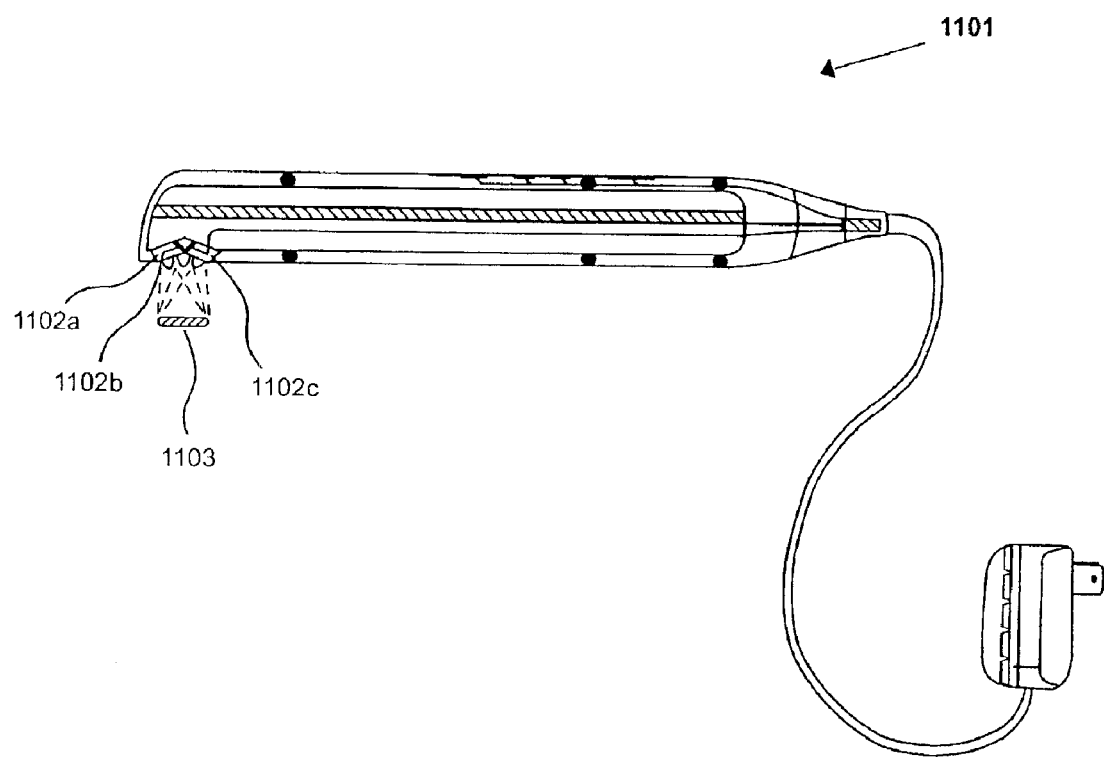
FIG. 12 depicts a cross section of the light of FIG. 11.

FIG. 11 depicts an AC-powered curing light 1101 that uses three light emitting diode chips or modules as a light source. FIG. 12 depicts a cross-section of the light 1101 of FIG. 11. The componentry of this curing light is as generally described previously except for its three light emitting diode light source structure. It uses three light emitting diode chips or chip modules 1102a, 1102b and 1102c arranged in complementary angled configuration so that the light beams emitted by each overlap at a desired distance from the light source to form an overlapped and enhanced intensity light footprint 1103.

Figure 13:
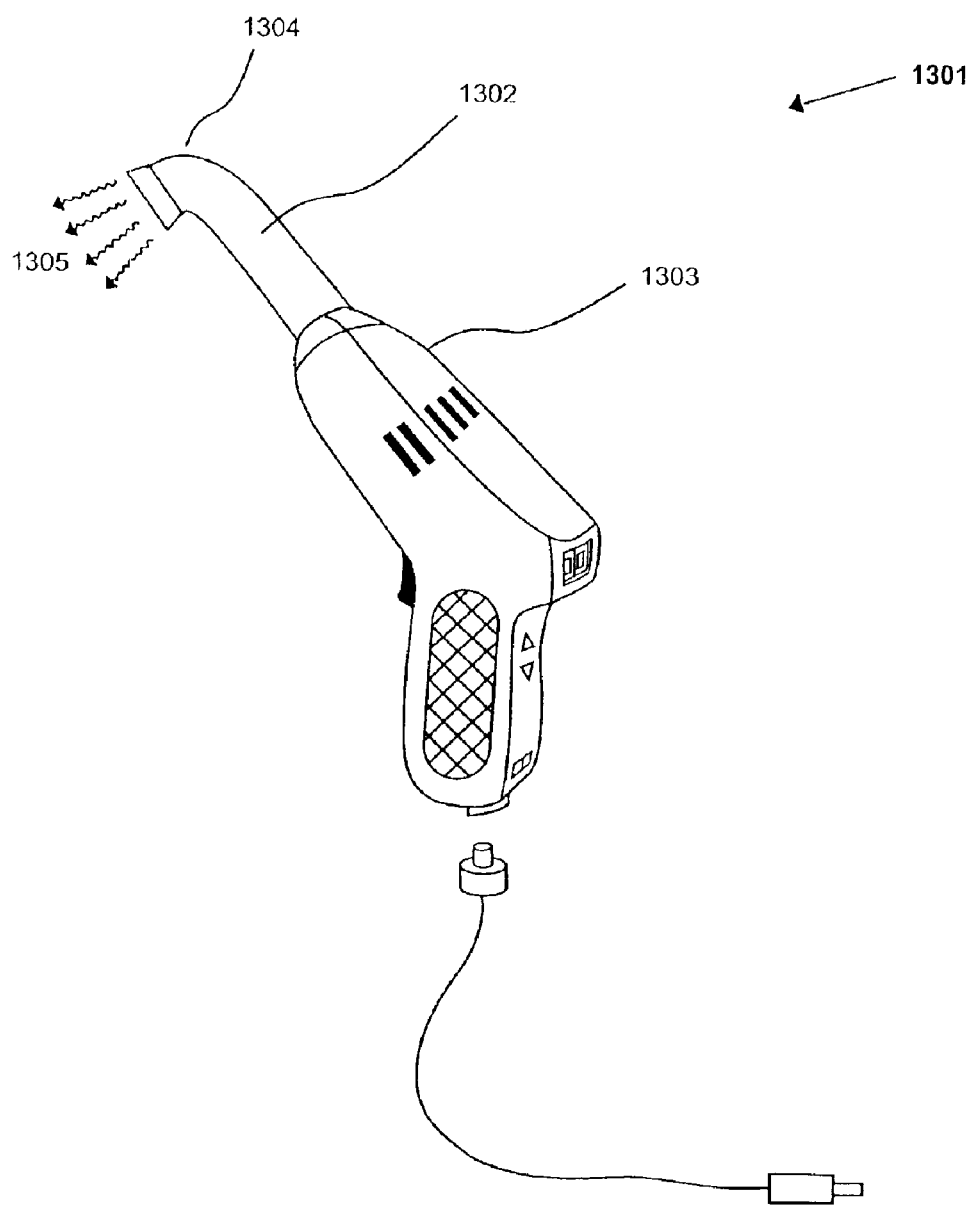
FIG. 13 depicts a battery-powered curing light that uses three or more semiconductor chip modules mounted on a heat sink in a manner that the light they emit is collected by a reflector apparatus and focused by a lens means onto a light transport mechanism, such as a light guide, plastic stack or fiber.
Figure 14:
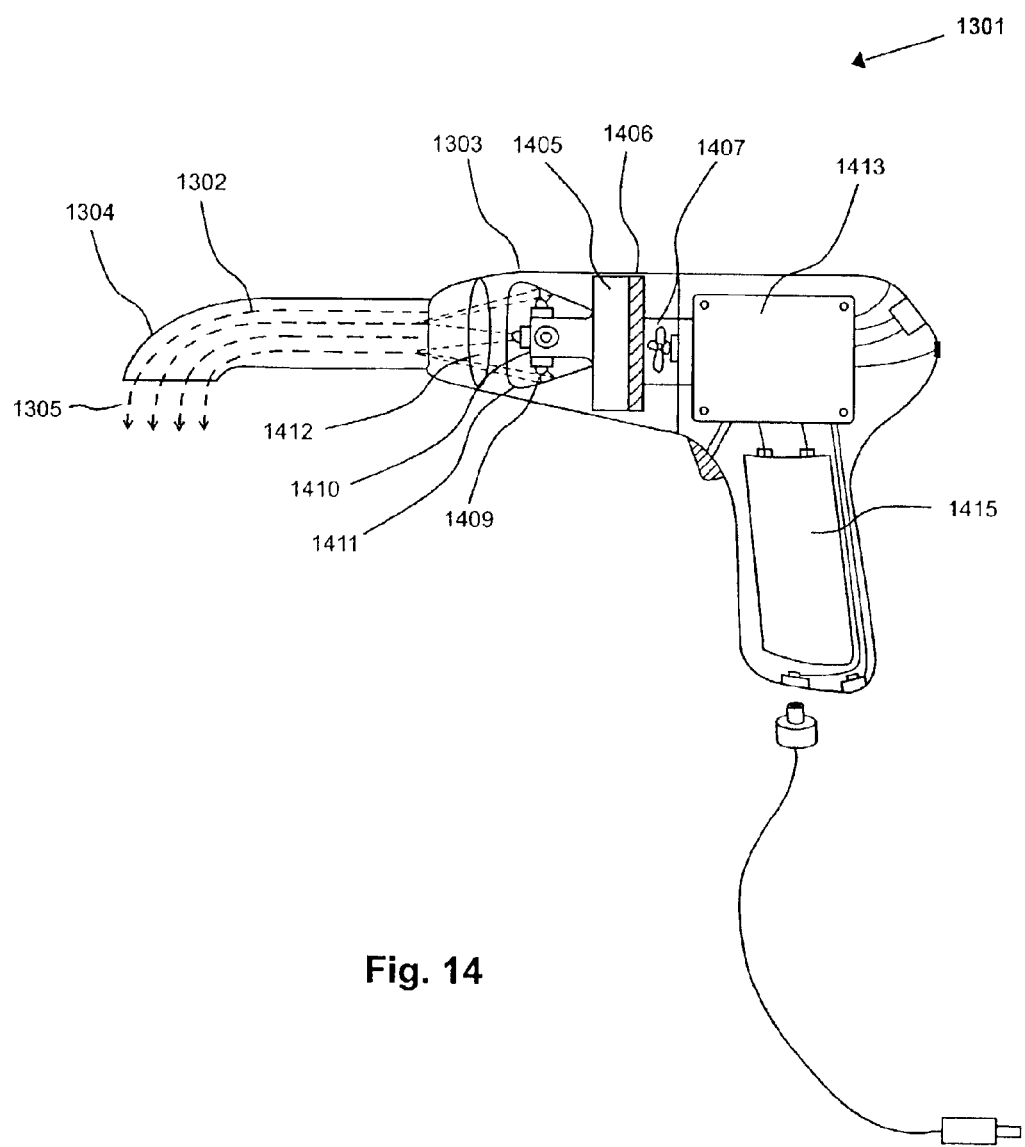
FIG. 14 depicts a cross-section of the light of FIG. 13.

FIG. 13 depicts a battery-powered curing 1301 light that uses a plurality of semiconductor chip modules mounted on a heat sink in a manner that the light they emit is collected by a reflector apparatus and focused by a lens means onto a light transport mechanism, such as a light guide, plastic stack or fiber 1302. FIG. 14 depicts a cross-section of the light 1301 of FIG. 13. Many of the components of this light are as discussed previously for other curing light embodiments, and that discussion is not repeated here. However, the light source and light transport means are very different from embodiments discussed above. The curing light 1301 includes a housing 1303 which has a light transport means 1302 such as a light guide, plastic stack or fiber attached to it. The light transport means 1302 transports light from a light module to a remote location for use. The light transport means 1302 depicted has a curved distal portion 1304 to cause light 1305 to be emitted in a desired direction, such as at a right angle to the longitudinal axis of the curing light or the light transport means. The light transport means may be removable and replaceable with light guides of different lengths and configurations. A gross or secondary heat sink 1405 is provided for heat removal from the system. The secondary heat sink 1405 has a proximal side on which a thermoelectric material layer 1406 may be placed to enhance heat removal ability. Optionally, a fan 1407 may be provided to improve heat removal efficiency, and vents may be provided in the housing to encourage air circulation. The secondary heat sink 1405 may have mounted directly or indirectly to it a plurality of semiconductor light emitting chips or chip modules 1409. Those chips 1409 may be mounted to a primary heat sink such as 1410. Light emitted by the chips 1409 will be reflected by a reflector device 1411 such as a mirrored parabolic reflector to an optional lens or focusing device 1412 which focuses a generally coherent light beam onto the light transport means 1302. The reflector may be of a desired shape for directing light, such as frusto-conical, parabolic or otherwise. If the light emitting devices are oriented so that the light which they emit is substantially directed toward the distal end of the curing light, the reflector may be omitted. A battery pack 1415 and control circuitry 1413 are provided.

Figure 15:
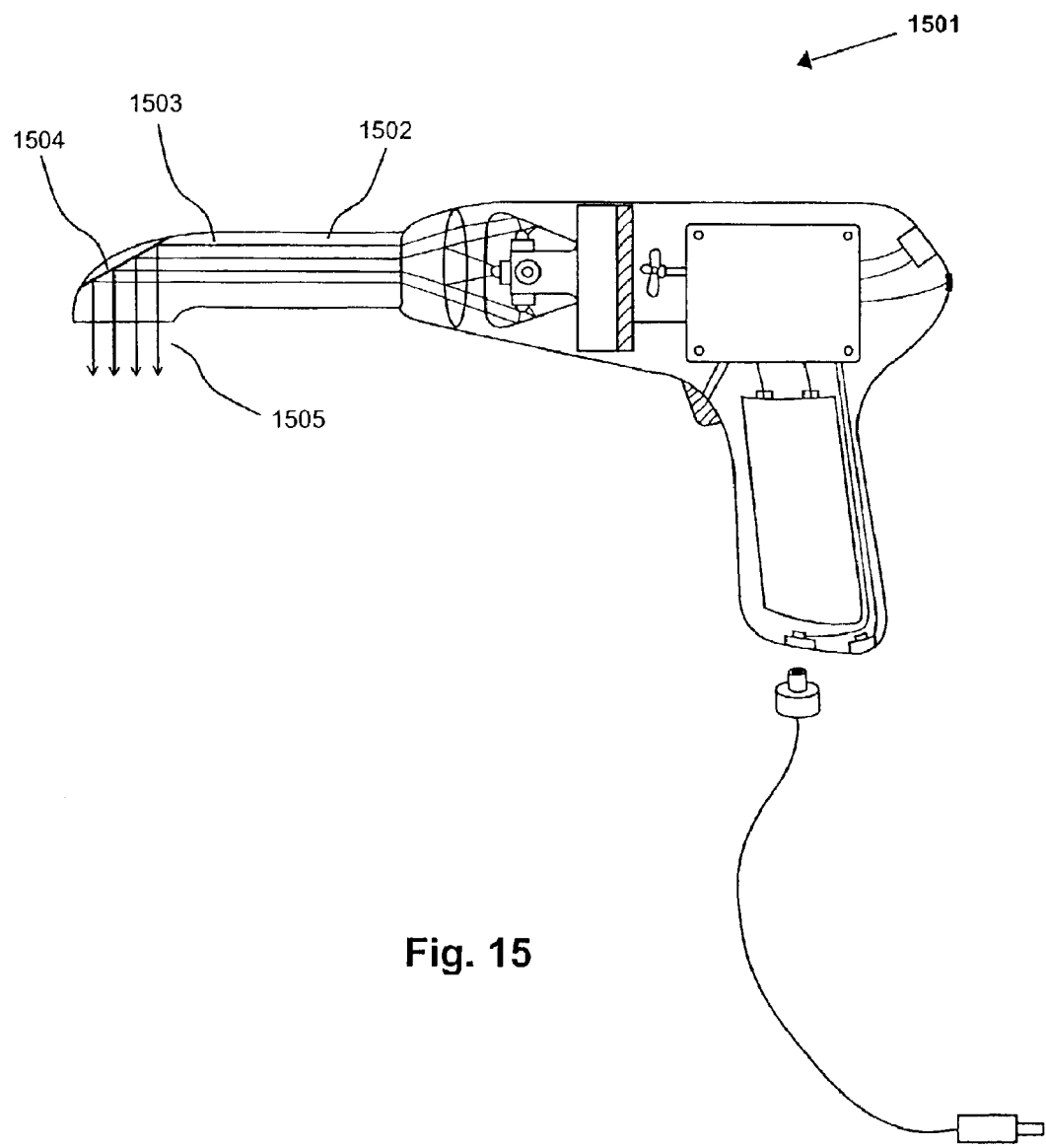
FIG. 15 depicts an alternative embodiment of the light of FIG. 13, in the light transport mechanism is replace by a distally-located mirror which reflects generally coherent light emitted from the light source in a desired direction for use.

FIG. 15 depicts an alternative embodiment of the light of FIG. 13. The curing light 1501 has no light transport mechanism and instead has a light exit tube 1502 that has a distal end with a mirror or reflector 1504 which can reflect a generally coherent light beam 1503 to a light exit 1505 in a desired direction for use, such as at a generally right angle to the longitudinal axis of the light module or the curing light.

Figure 16A:
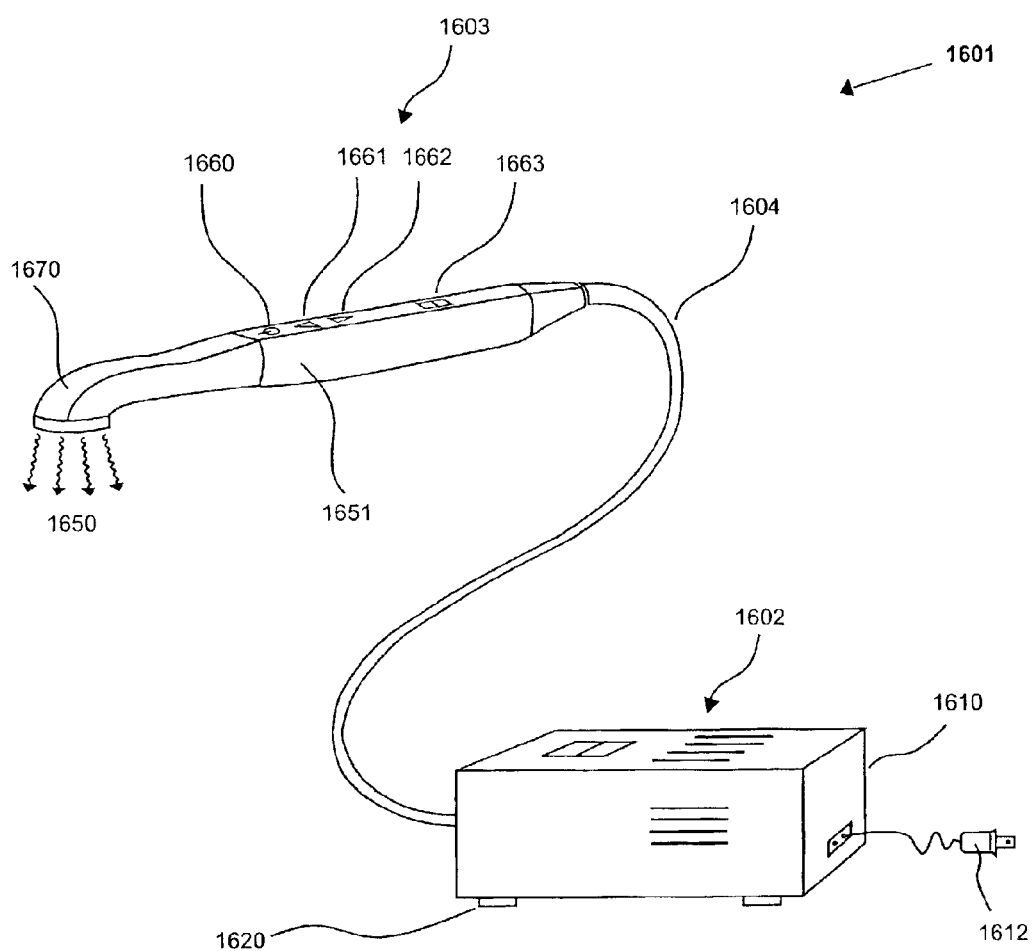
FIG. 16a depicts a light which uses a plurality of light emitting semiconductor modules mounted on a heat sink as a light source, a focusing means to produce a generally coherent beam of light, and a light transport means such as optically conductive cable for transporting light to a location remote from the light source for use.
Figure 16B:
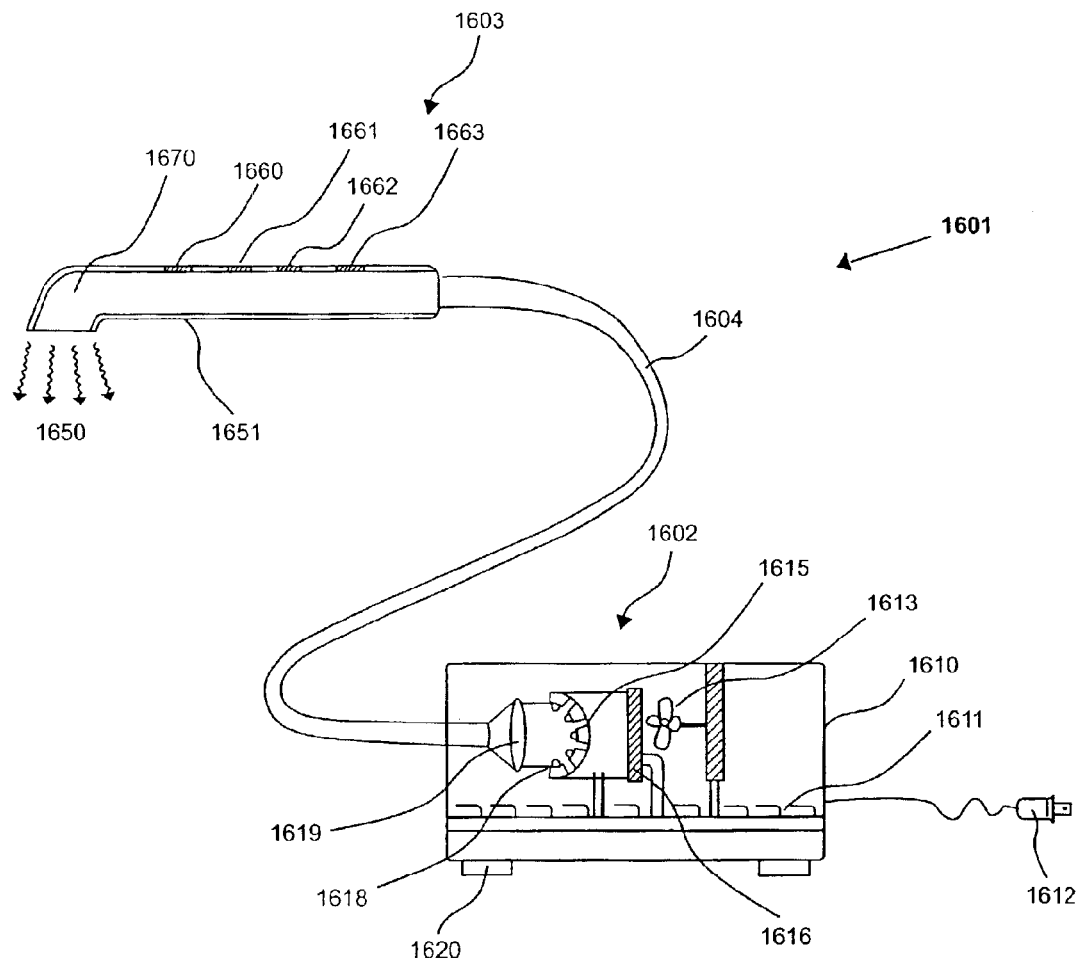

FIG. 16a depicts a curing light curing light 1601 that has a light source and control module 1602 remotely located from a handpiece 1603 connected by a connection means 1604 that includes an optically conductive cable and electrical wires for electrical connection. FIG. 16b depicts a cross section of the light of FIG. 16a. The light source and control module 1602 includes a housing 1610 with optional air vents thereon, electronic control circuitry 1611, an electrical cord with power plug 1612, a cooling fan 1613 for air circulation and heat dissipation, a heat sink 1615 which may be appropriately shaped to accept light emitting semiconductor devices on its distal side, such as having a concave hemispherical or parabolic portion, and having a thermoelectric cooler 1616 on its proximal side for enhanced heat dissipation. A plurality of light emitting semiconductor devices such as LED chip modules 1618 are mounted to the heat sink distal side so that they emit light into an optical system such as a focus lens 1619 which places a generally coherent light beam onto the optically conductive cable where it is transported to a distant handpiece 1603 that includes a housing 1651, light exit 1650 for permitting light to be delivered to a composite material to be cured, and various controls such as light on/off control 1660, timer display 1663, and timer adjustment buttons 1661 and 1662. The distal end of the handpiece housing 1670 may be angled from the longitudinal axis of the handpiece in for convenience of light application to a composite material.

As desired in various embodiments of the inventions, the light source may be a single LED chip, single LED chip array, an array of LED chips, a single diode laser chip, an array of diode laser chips, a VCSEL chip or array, or one or more LED or diode laser modules. The wavelength of light emitted from the semiconductor light source can be any desired wavelength or combination of different wavelength, depending on the sensitivity of the photoinitiator(s) in the composite material to be cured. Any of the semiconductor and heat sink arrangements described herein may be used to construct desired curing lights.

Figure 17A:
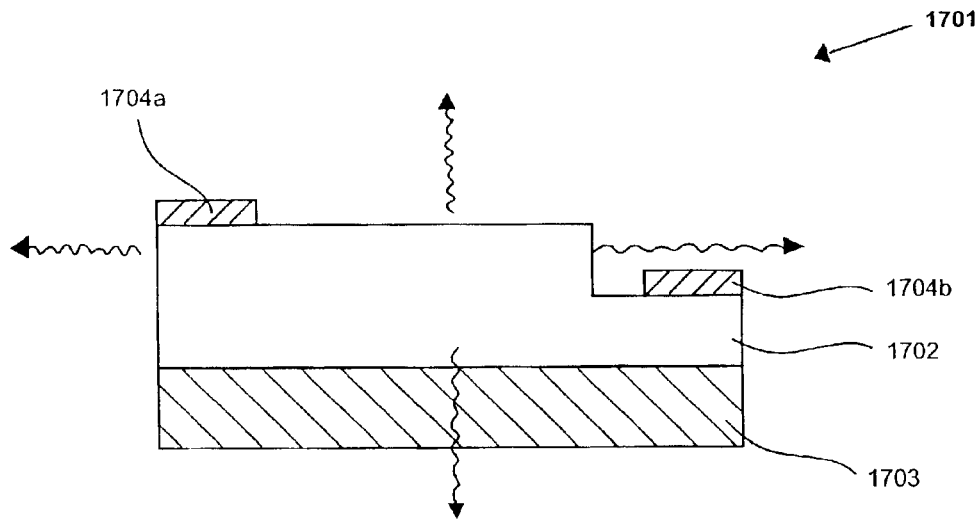
FIG. 17a depicts a gross cross section of a light emitting diode chip that uses an insulative substrate.

Referring to FIG. 17a, a light emitting diode ("LED") chip 1701 is depicted in which the LED structure 1702 has been grown on top of or on one side of an insulative substrate 1703. Electrodes 1704a and 1704b are provided to power the LED. In such a structure, all electrodes will be located on the top surface of the LED. Light is emitted from all sides of the LED as depicted.

Figure 17B:
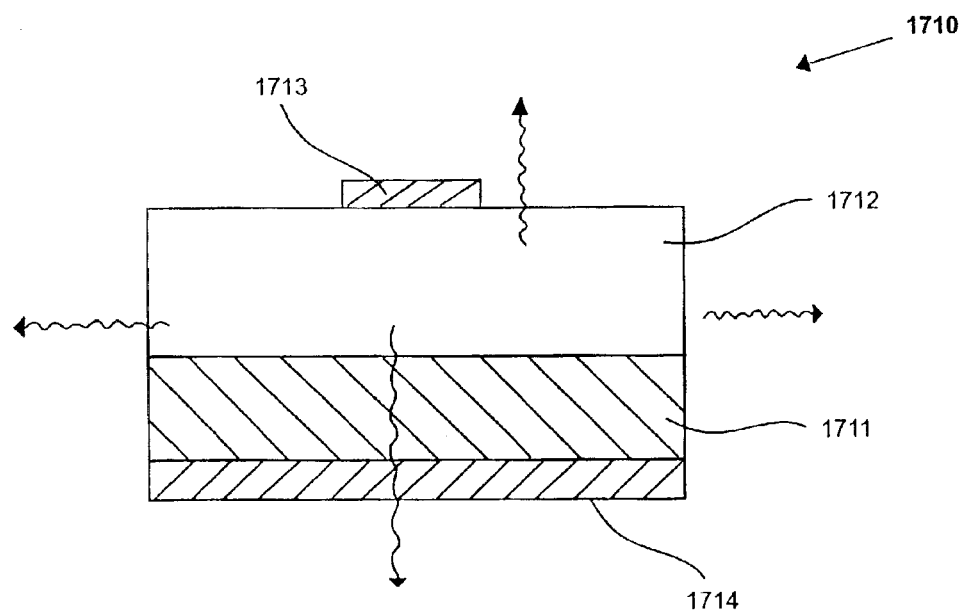
FIG. 17b depicts a gross cross section of a light emitting diode chip that uses a conductive substrate.

A similar LED chip 1710 with a conductive substrate 1711 and accompanying LED structure 1712 and electrodes 1713 and 1714 is depicted in FIG. 17b.

Figure 18A:
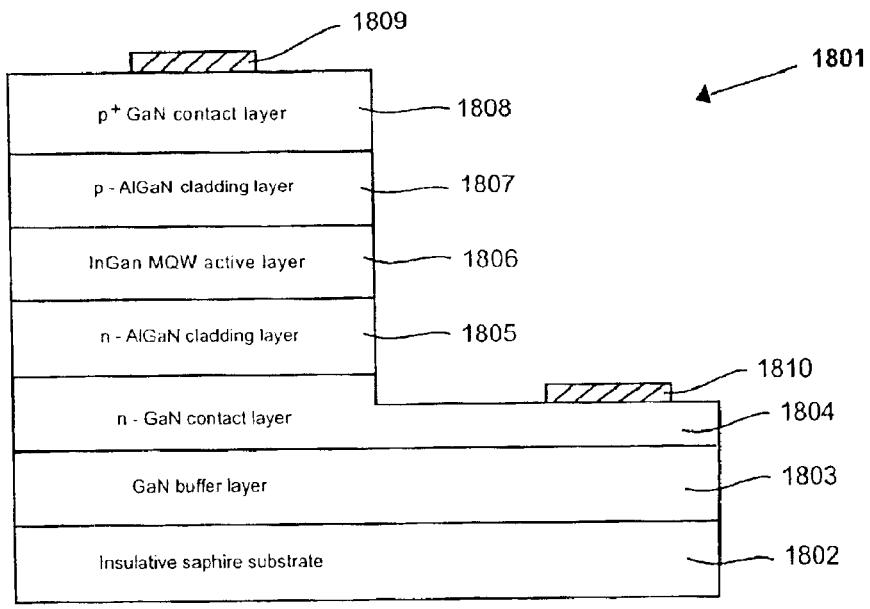
FIG. 18a depicts epitaxial layers of a light emitting diode chip that uses an insulative substrate.

FIG. 18a depicts an example of epitaxial layer configuration 1801 for an LED with an insulative substrate used in the invention. The LED includes an electrically insulative substrate such as sapphire 1802. The substrate serves as a carrier, pad or platform on which to grow the chip's epitaxial layers. The first layer placed on the substrate 1802 is a buffer layer 1803, in this case a GaN buffer layer. Use of a buffer layer reduces defects in the chip which would otherwise arise due to differences in material properties between the epitaxial layers and the substrate. Then a contact layer 1804, such as n-GaN, is provided. A cladding layer 1805 such as n-AlGaN Sub is then provided. Then an active layer 1806 is provided, such as InGaN multiple quantum wells. The active layer is where electrons jump from a conduction band to valance and emit energy which converts to light. On the active layer 1806, another cladding layer 1807, such as p-AlGaN is provided that also serves to confine electrons. A contact layer 1808 such as p+ GaN is provided that is doped for Ohmic contact. The contact layer 1808 has a positive electrode 1809 mounted on it. The contact layer 1804 has a negative electrode 1810.

Figure 18B:
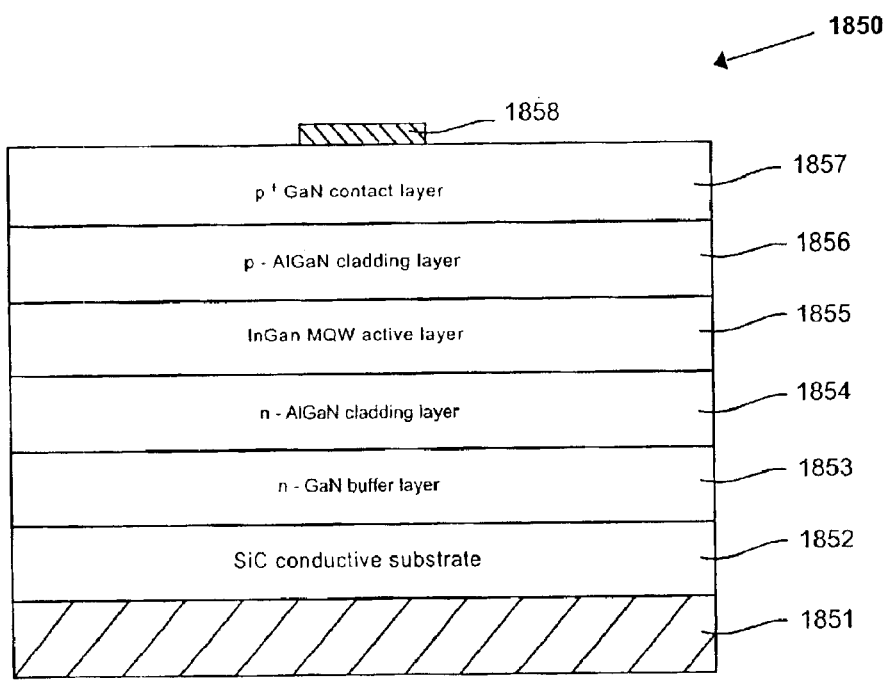
FIG. 18b depicts epitaxial layers of a light emitting diode chip that uses a conductive substrate.

FIG. 18b depicts epitaxial layer configuration 1850 for an LED with a conductive substrate. The LED includes an electrically conductive substrate such as SiC 1852 that has an electrode 1851 on it. The substrate serves as a carrier, pad or platform on which to grow the chip's epitaxial layers, and as a negative electrode in the chip. The first layer placed on the substrate 1852 is a buffer layer 1853, such as n-GaN. A cladding layer 1854 such as n-AlGaN is provided followed by an active layer 1855 such as InGaN with multiple quantum wells. That is followed by a cladding layer 1856 such as p-AlGaN and finally a contact layer 1857 such as p+ GaN that has an electrode 1858 mounted on it.

Figure 19A:
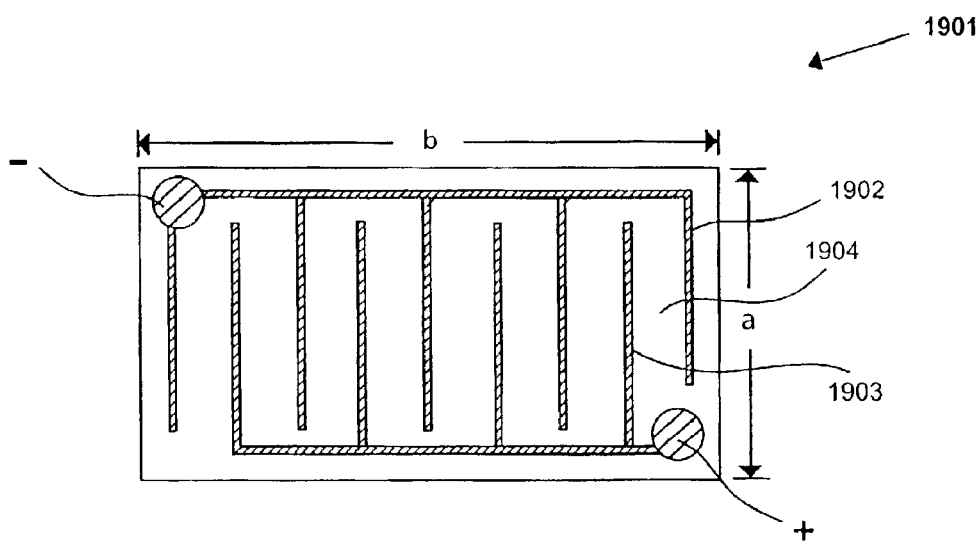
FIG. 19a depicts a top view of a light emitting diode chip array (single chip) with an insulative substrate.

FIG. 19a depicts a top view of an LED array on a single chip 1901 with a size a×b on an insulating substrate. The size of a and b are each greater than 300 micrometers. Semiconductor materials 1904 are located on an electrically insulative substrate (not shown). Positive and negative electrode pads are provided, each in electrical connection with its respective metal electrode strip 1902 and 1903 arranged in a row and column formation (8 columns shown) to create the array and power the chip. This structure enables the LED to emit light of greater power than that which is possible in a non-array traditional chip.

Figure 19B:
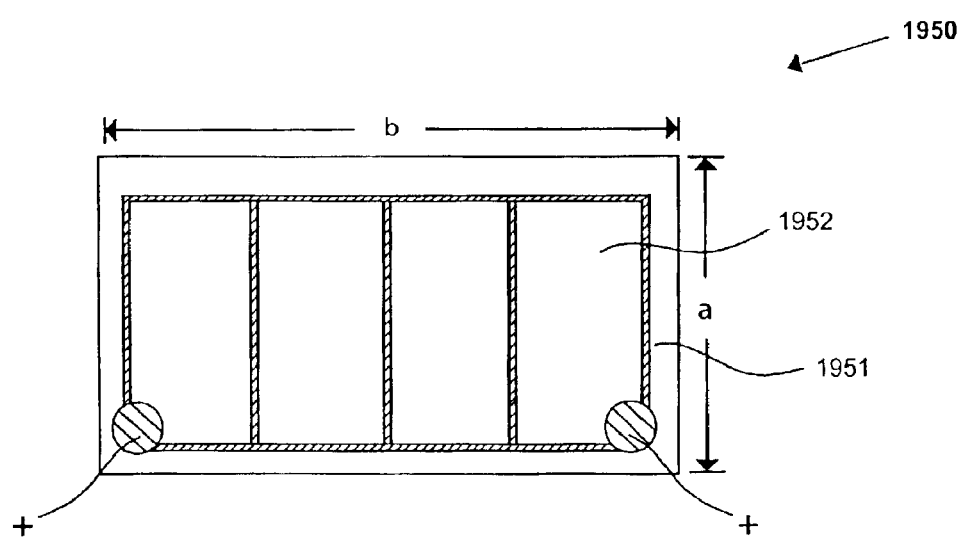
FIG. 19b depicts a top view of a top view of a light emitting diode chip array (single chip) with a conductive substrate.

FIG. 19*b* depicts a top view of an LED array on a single chip 1950 with a size a×b on a conductive substrate. Each of sizes a and b is greater than 300 micrometers. Semiconductor materials 1952 are located on an electrically conductive substrate (not shown). Positive electrode pads are provided in electrical connection with a metal strip 1951 arranged in an array formation to power the chip. The substrate serves as the negative electrode in the embodiment depicted.

Figure 20A:
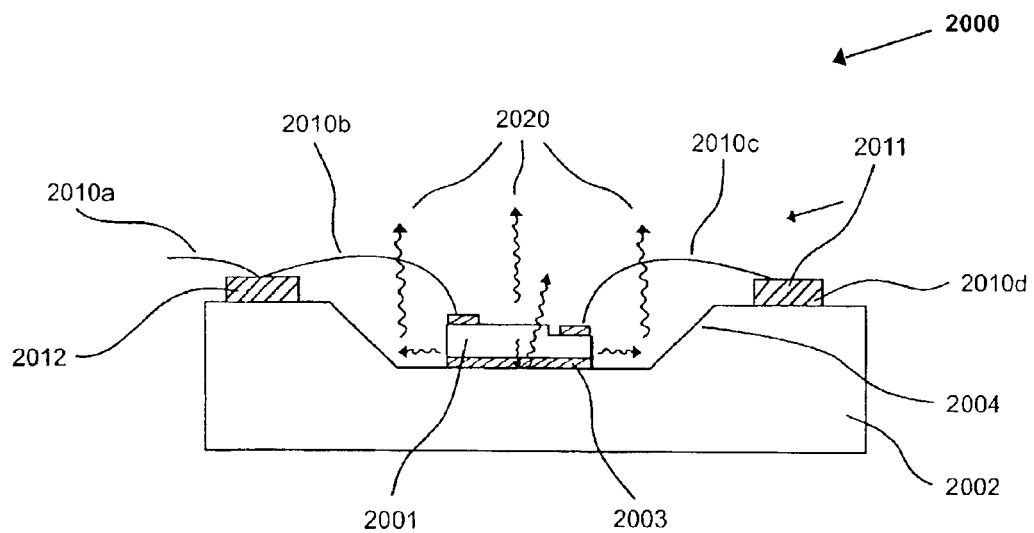
FIG. 20a depicts a side view of a chip package for a light emitting chip that shows a light emitting diode chip with an insulative substrate mounted in a well of a heat sink, with electrical connections and light emission shown.

Referring to FIG. 20*a,* a side view of a surface mount LED chip package 2000 including the LED chip 2001 on a heat sink 2002 is provided. The LED chip depicted has an insulating substrate and is mounted in a well 2004 of the heat sink 2002 by the use of heat conductive and light reflective adhesive 2003. Light is emitted by the chip in all directions, and light which is emitted toward the adhesive 2003 or the well walls is reflected outward in a useful direction 2020. The chip is electrically connected via wires 2010*a,* 2010*b,* 2010*c* and 2010*d* using intermediary islands 2011 and 2012. The LED chip is located in a circular well 2004 of the heat sink 2002. The circular well is formed with sides or walls at about a 45 degree angle or other desired angle (such as from about 170 to about 10 degrees) so that light emitted from the side of the chip will be reflected from the walls of the well in a desired direction as indicated by arrows in the figure. This allows the highest possible light intensity to be obtained using a chip of given size. The well walls may have a light reflective coating to increase efficiency.

Figure 20B:
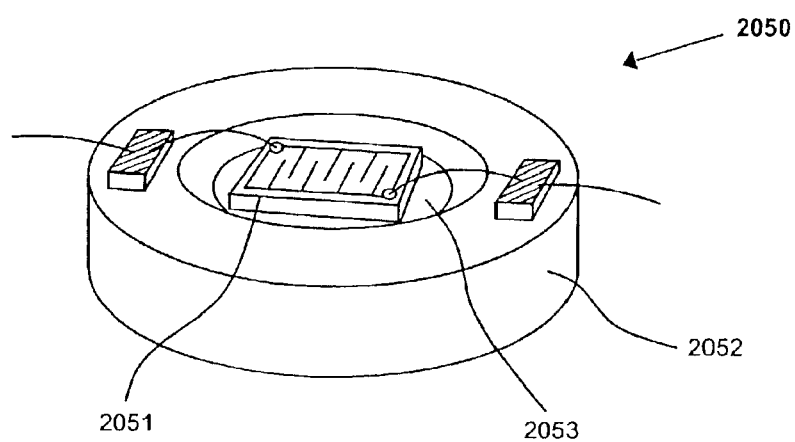
FIG. 20b depicts a perspective view of a chip package for a light emitting chip with an insulative substrate that shows a chip array mounted in a well of a heat sink.

Referring to FIG. 20*b,* a perspective view of a LED chip array (single chip) chip package 2050 including the chip array 2051 on an insulative substrate in a well 2052 of a heat sink 2053 is depicted.

Figure 21A:
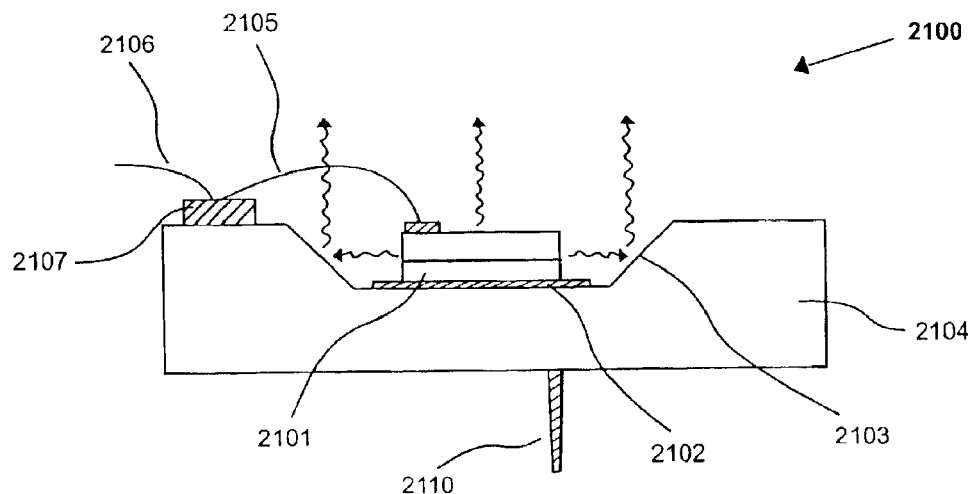
FIG. 21a depicts a side view of a chip package for a light emitting chip that shows a light emitting diode chip with a conductive substrate mounted in a well of a heat sink, with electrical connections and light emission shown.

Referring to FIG. 21*a,* a side view of an LED chip module 2100 is provided. An LED chip 2101 with a conductive substrate is mounted in a circular well 2103 of a heat sink 2104 by use of heat conductive light reflective adhesive 2102. A negative electrode 2110 is provided on the heat sink. Positive electrical connection is provided by wires 2105 and 2106, and island 2107.

Figure 21B:
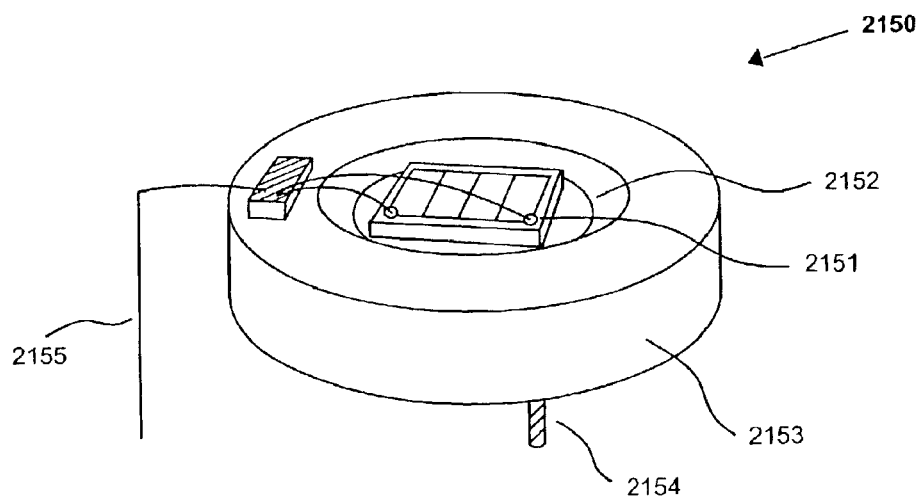
FIG. 21b depicts a perspective view of a chip package for a light emitting chip with a conductive substrate that shows a chip array mounted in a well of a heat sink.

Referring to FIG. 21*b,* a chip array package 2150 that includes an LED chip array 2151 with a conductive substrate mounted in a well 2152 of a heat sink 2153 with an electrode 2154 and wire connection 2155 is depicted.

Figure 22A:
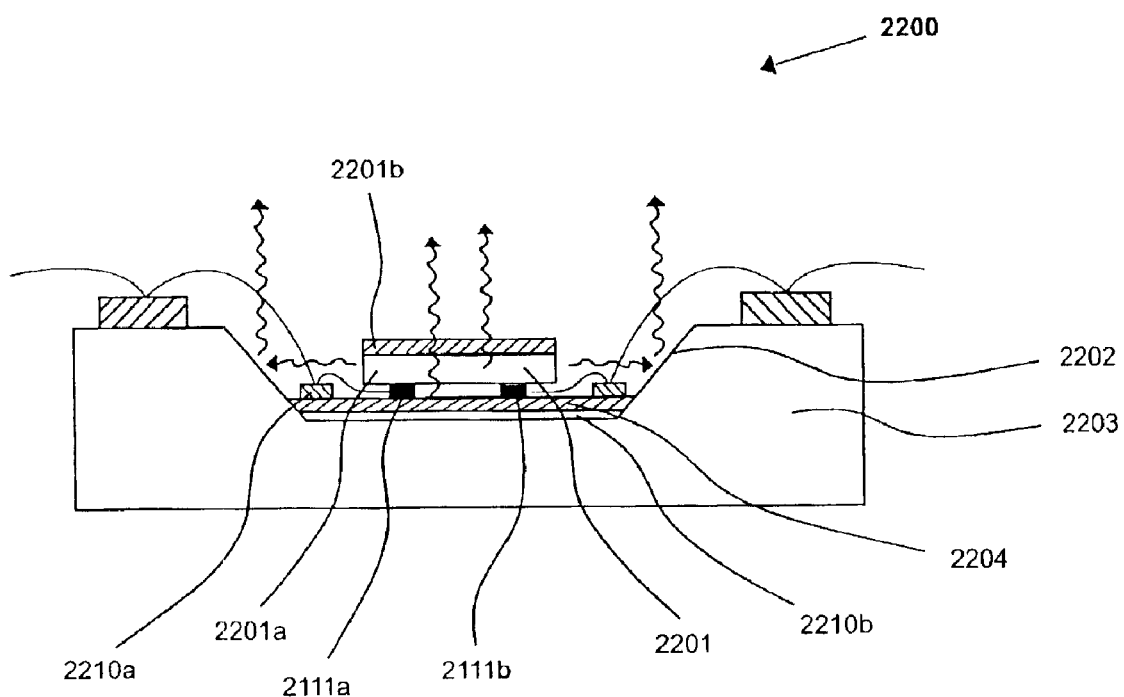
FIG. 22a depicts a side view of a chip package for a light emitting chip mounted in a well of a heat sink according to the so-called 'flip chip' design, the chip having an insulative substrate.
Figure 22B:
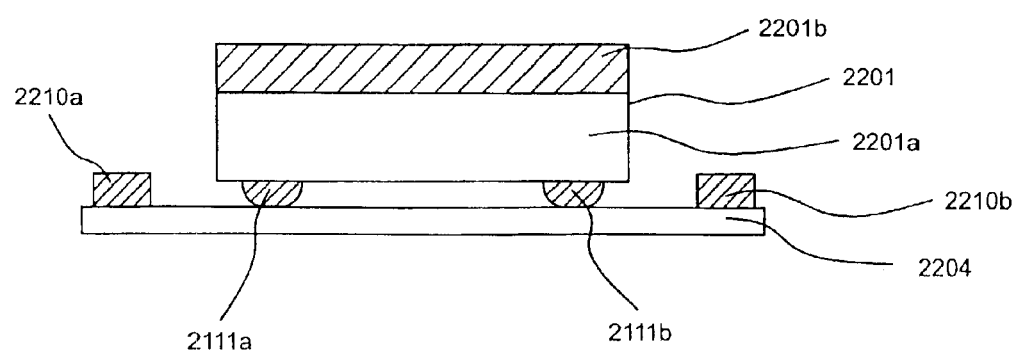
FIG. 22b depicts a side view of a flip chip mounted on a flip chip pad.
Figure 22C:
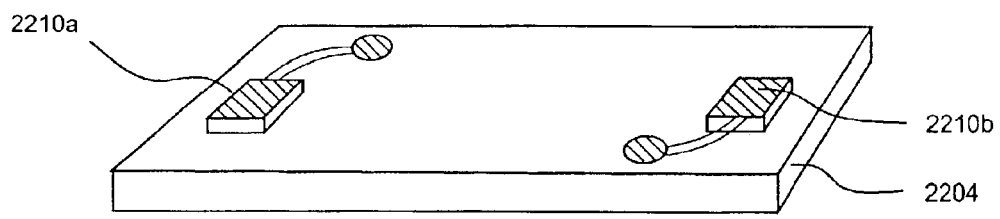
FIG. 22c depicts a perspective view of a flip chip pad.
Figure 22D:
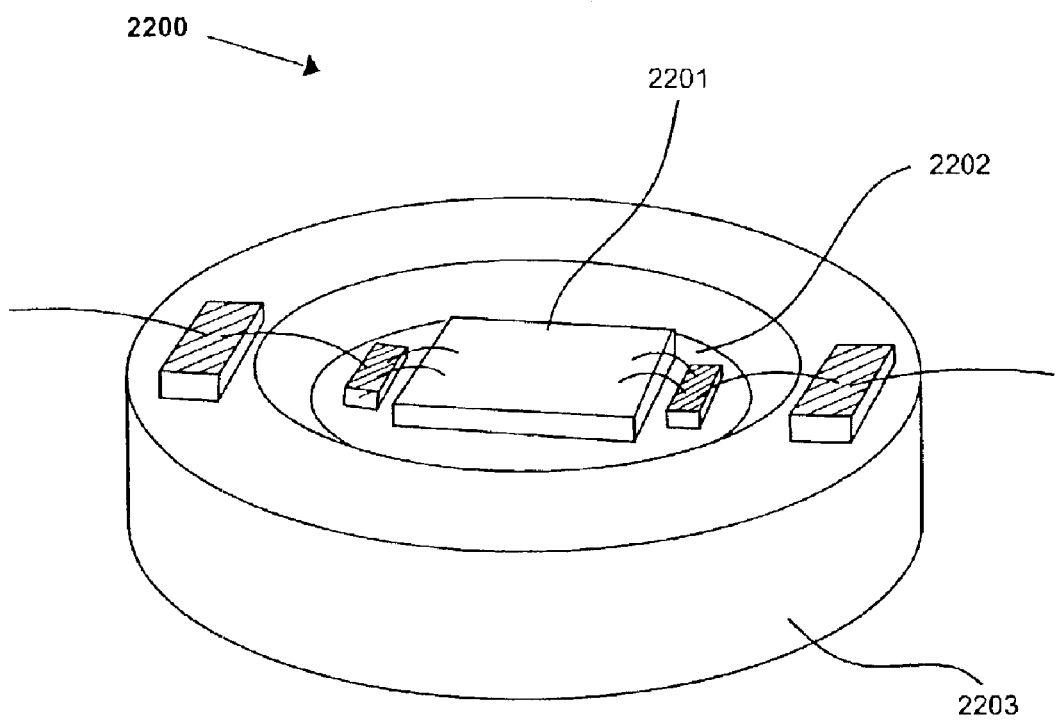

FIG. 22*a* depicts a side view of a chip package 2200 for a light emitting diode chip array 2201 mounted in a well 2202 of a heat sink 2203 according to the so-called 'flip chip' design, the chip having an insulative substrate. FIG. 22*b* depicts a side view of a flip chip 2201 mounted on a flip chip pad 2204. FIG. 22*c* depicts a perspective view of a flip chip pad 2204. FIG. 22*d* depicts a perspective view of the chip package 2200 of FIG. 22*a.* Intermediate islands or electrode pads 2201*a* and 2210*b* are provided on the flip chip pad to ease of electrical connection with the chip. Electrode bumps 2111*a* and 2111*b* are provided between the chip and the pad for electrical connection. The chip has an electrode 2201*b* on top and its epitaxial layers 2201*a* facing down toward the pad 2204 and the bottom of the well 2202. The pad 2204 upper surface is light reflective so that light is reflected from the pad in a useful direction. The pad 2204 may be coated with a light reflective film, such as Au, Al or Ag. In such a package, all of the light emitted from the chip can be reflected back in the light exit direction for highest light output.

Figure 23:
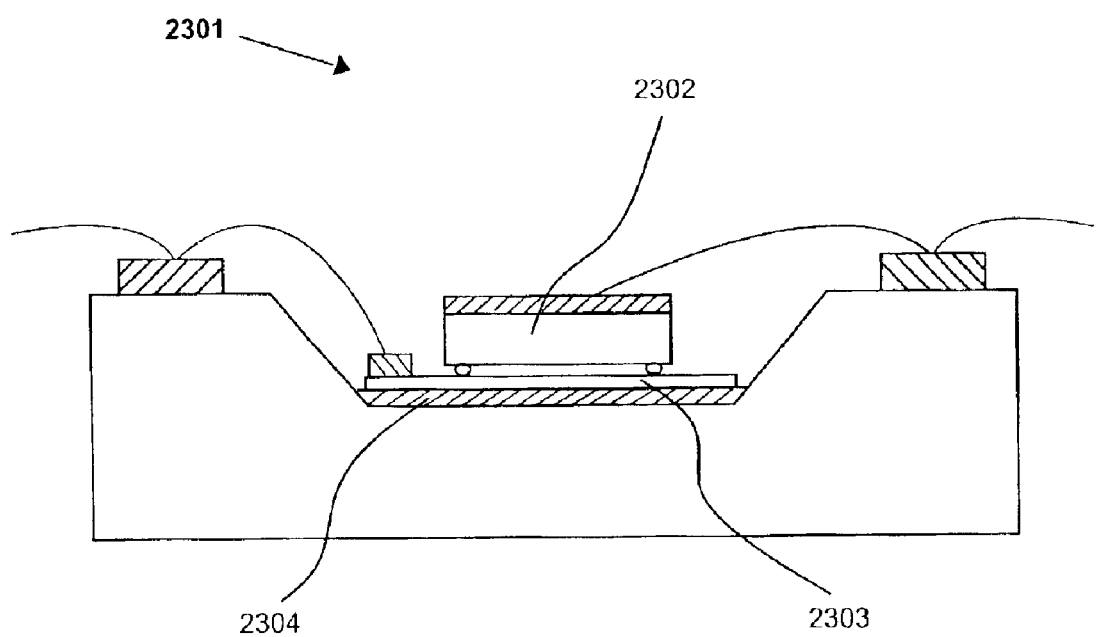
FIG. 23 depicts a side view of a flip chip package with a conductive susbtrate.

FIG. 23 depicts a flip chip package 2301 in which a chip 2302 with a conductive substrate is mounted upside down (electrode up) on a flip chip pad 2303 with light reflective and heat conductive adhesive 2304 in the well of a heat sink. Electrical connection takes advantage of the exposed electrode of the chip 2302.

Figure 24A:
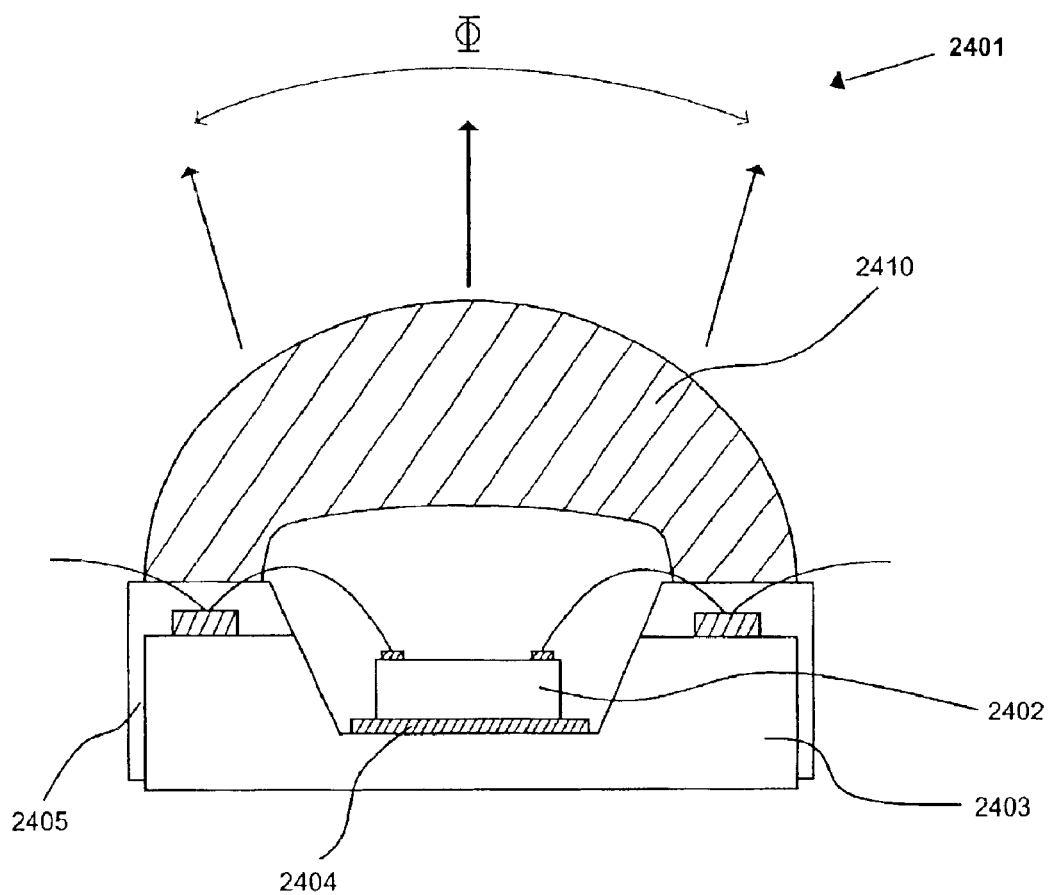
FIG. 24a depicts a side view of a light emitting diode chip package including the chip (insulative substrate) and heat sink surface mount arrangement with a protective dome, lens or cover.
Figure 24B:
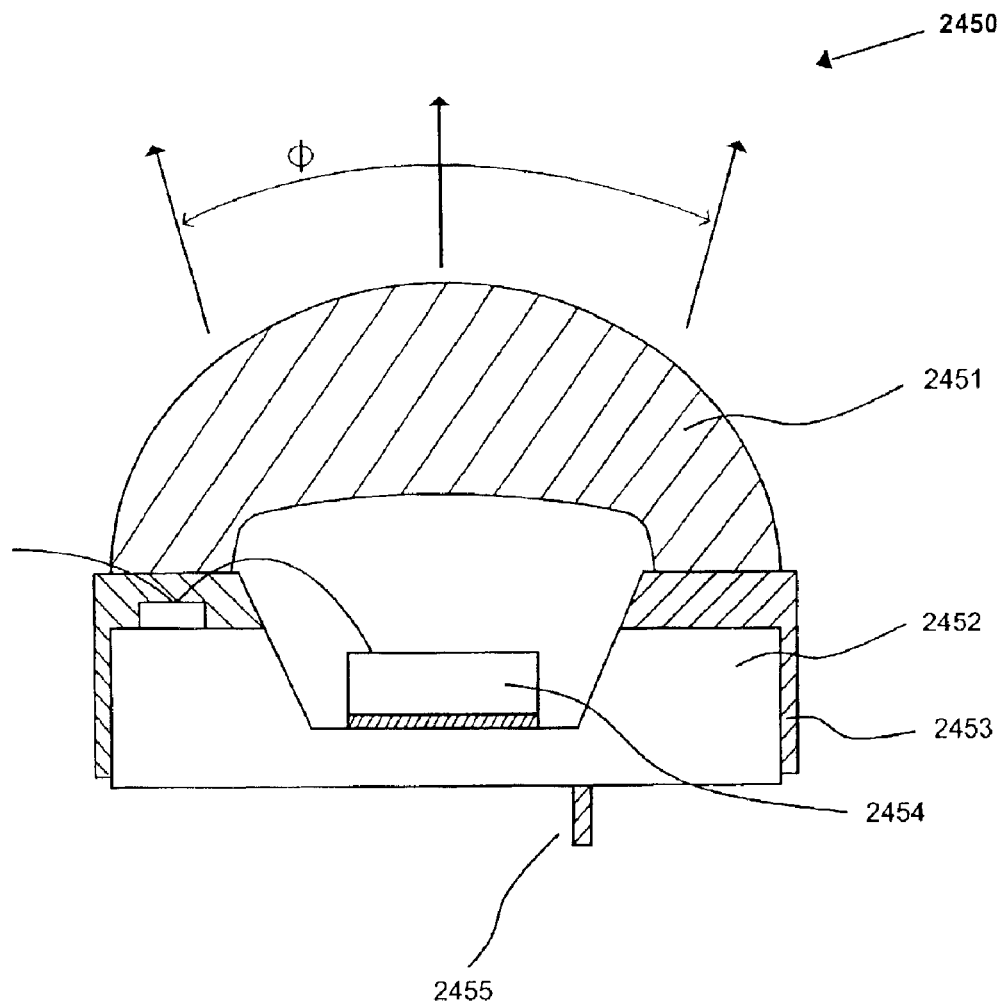
FIG. 24b depicts a side view of a light emitting diode chip package including the chip (conductive substrate) and heat sink surface mount arrangement with a protective dome, lens or cover.

Referring to FIG. 24*a,* a high power LED package 2401 is depicted using a chip 2402 with an insulative substrate mounted in the well of a heat sink 2403 using heat conductive and light reflective adhesive 2404. The heat sink is surrounded by a known insulating material 2405 that serves the purpose of protecting electrode and dome connections. The walls and bottom of the well may be polished to be light reflective, or may be covered, plated, painted or bonded with a light-reflective coating such as Al, Au, Ag, Zn, Cu, Pt, chrome, other metals, plating, plastic and others to reflect light and thereby improve light source efficiency. Electrodes and/or connection blocks are provided for electrical connection of the chip. An optical dome or cover 2410 may optionally be provided for the purpose of protecting the chip and its assemblies, and for the purpose of focusing light emitted by the chip. The dome may be made of any of the following materials: plastic, polycarbonate, epoxy, glass and other suitable materials. The configuration of the well and the dome provide for light emission along an arc of a circle defined by $\phi$. FIG. 24*b* depicts a similar arrangement for a chip package 2450 in which the chip 2454 has a conductive substrate and thus when mounted to the heat sink 2452 can use an electrode 2455 on the heat sink itself for electrical connection. Protective dome 2451 and insulating covering 2453 are provided.

Figure 25A:
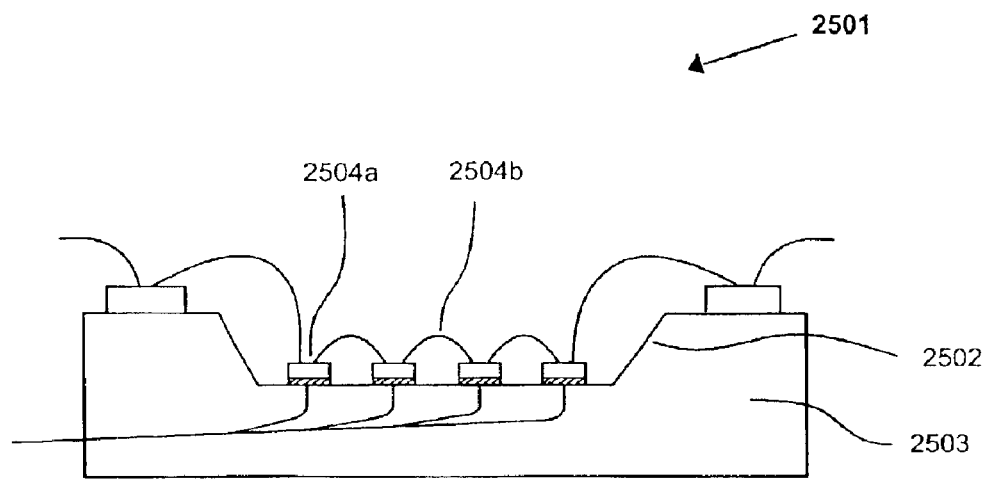
FIG. 25a depicts an array of light emitting chips with insulative substrates in surface mount arrangement in a single well of a heat sink.
Figure 25B:
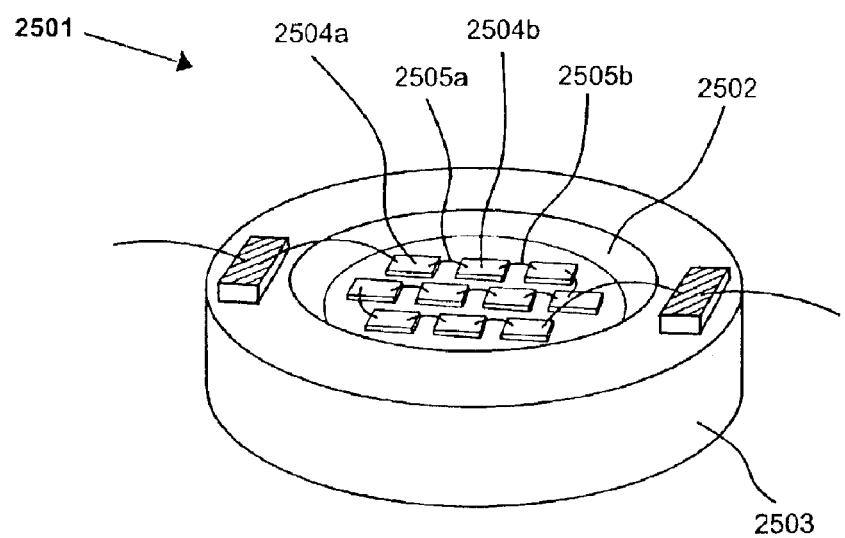

Referring to FIGS. 25*a* and 25*b,* a chip package 2501 is provided with an array of light emitting semiconductor chips 2504*a,* 2504*b,* etc. having electrically insulative substrates located in a single well 2502 of a heat sink 2503. The chips are mounted by an electrically conductive and heat conductive adhesive 2605. The chips are electrically connected to each other by wires 2505*a,* 2505*b,* etc.

Figure 26A:
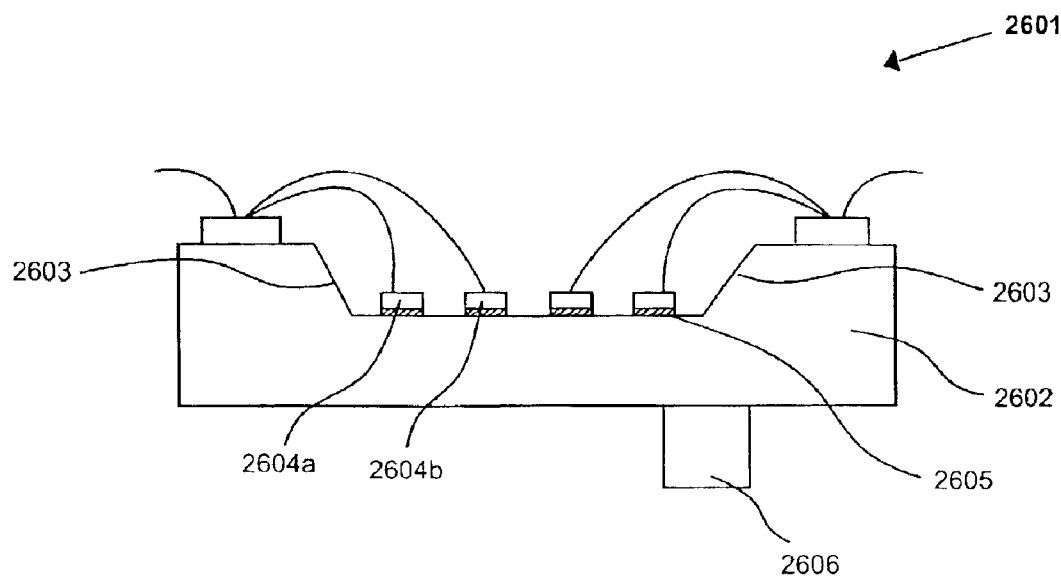
FIG. 26a depicts an array of light emitting chips with conductive substrates in surface mount arrangement in a single well of a heat sink.
Figure 26B:
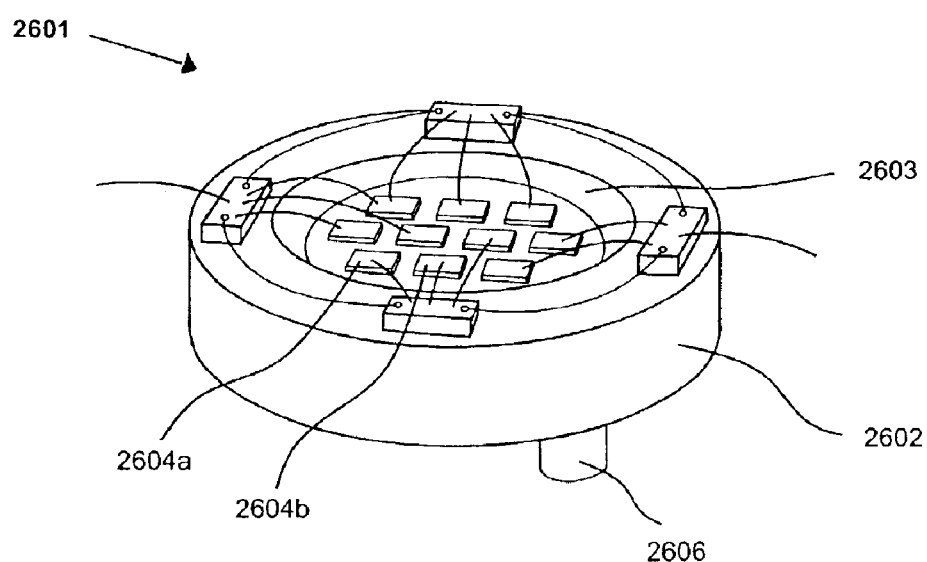

Referring to FIGS. 26*a* and 26*b,* a chip package 2601 is provided that has a heat sink 2602 with a single well 2603 and an array of LED chips 2604*a,* 2604*b,* etc. in the well 2603. The chips have electrically conductive substrates and an electrode 2606 is provided on the heat sink.

Figure 27A:
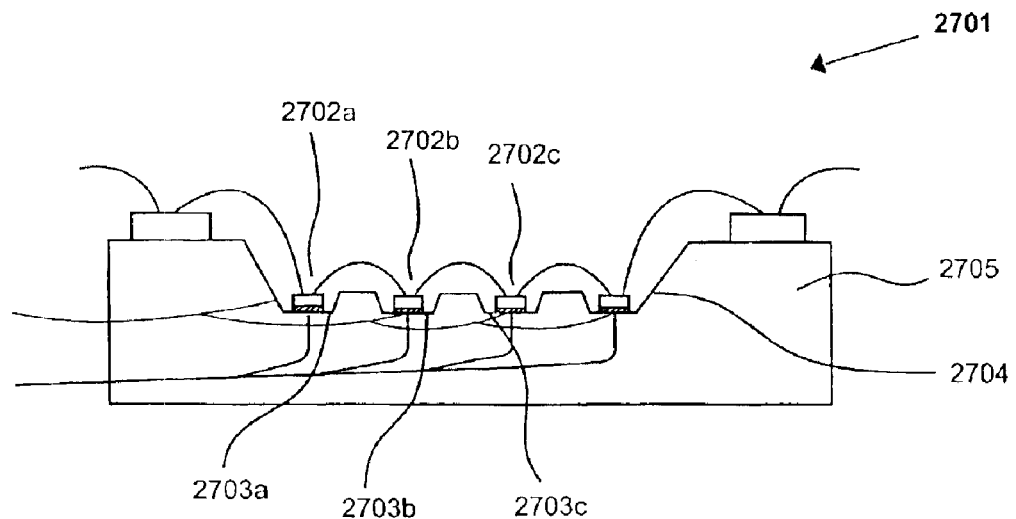
FIG. 27a depicts an array of light emitting chips with insulative substrates in surface mount arrangement in individual sub-wells of a well of a heat sink.

Referring to FIG. 27*a,* a chip package 2701 is depicted with an array of LED chips 2702*a,* 2702*b,* 2702*c,* etc. is depicted, with each chip located in its own individual sub-well 2703*a,* 2703*b,* 2703*c* in a gross well 2704 of a heat sink 2705. The chips have electrically insulative substrates.

Figure 27B:
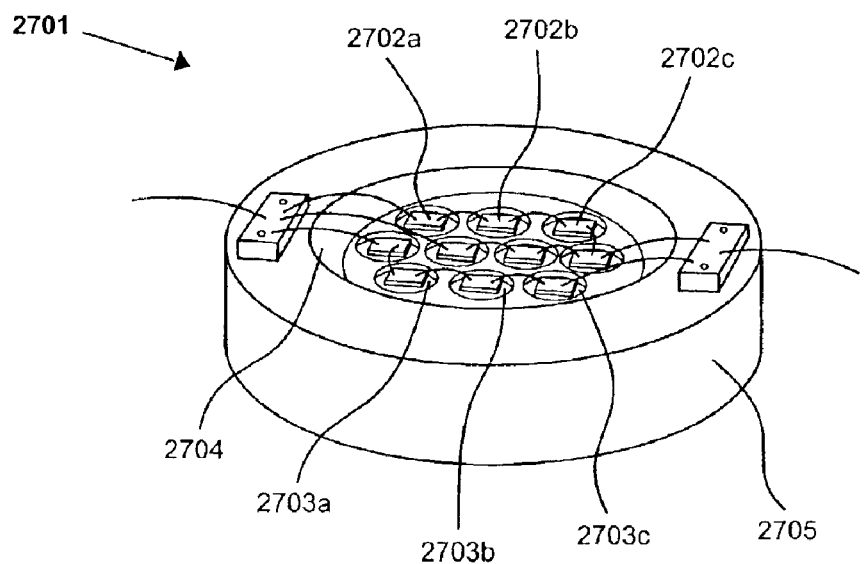

Referring to FIG. 27*b,* a chip package 2750 is depicted that has an array of LED chips 2763*a,* 2763*b,* 2763*c* with electrically conductive substrates. Each LED chip is mounted in its own individual sub-well, all located within a gross well 2761 of a heat sink 2762.

Figure 28A:
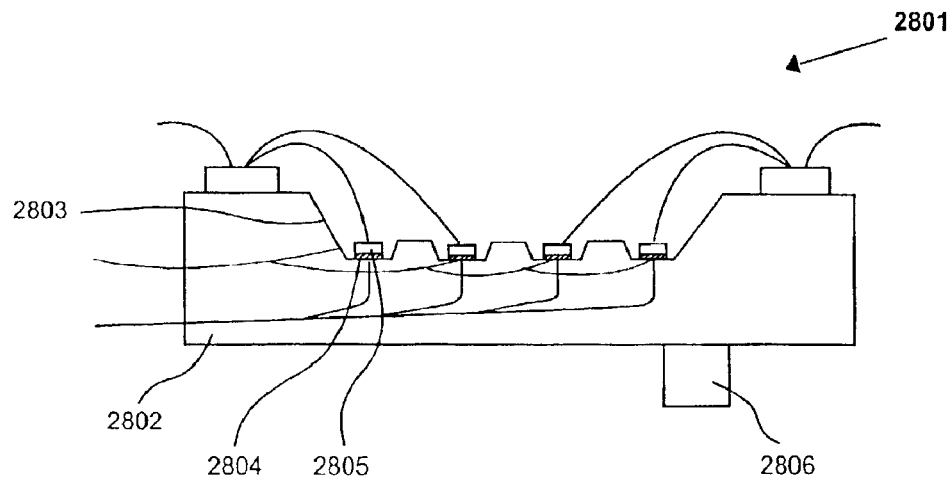
FIG. 28a depicts an array of light emitting chips with conductive substrates in surface mount arrangement in individual sub-wells of a well of a heat sink.
Figure 28B:
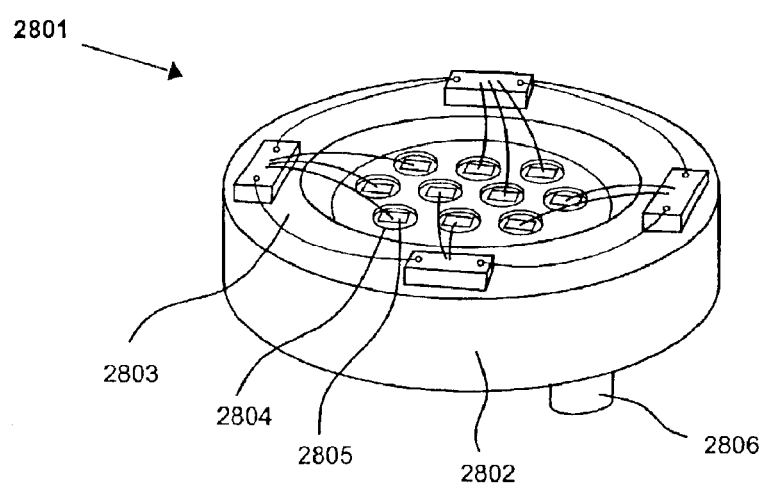

FIGS. 28*a* and 28*b* depict a chip package 2801 that has a heat sink 2802 with a gross well 2803 and a plurality of sub-wells 2804 therein, each sub-well having a light emitting chip 2805 with a conductive substrate within it. The heat sink 2803 has a negative electrode 2806 for electrical connection.

Figure 29A:
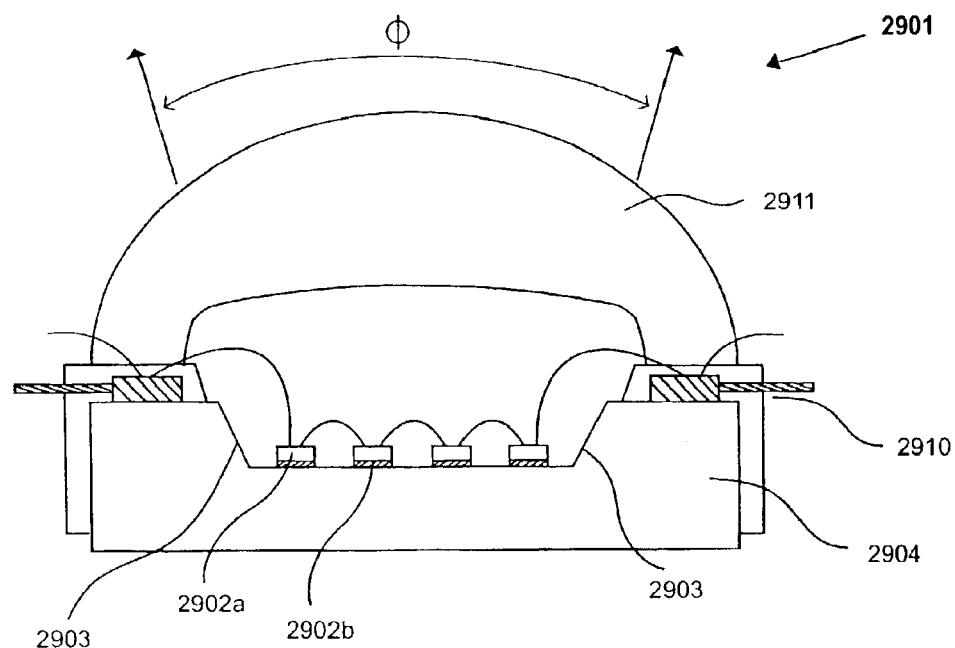
FIG. 29a depicts a light emitting surface mount chip package including array of chips, heat sink and protective dome, lens or cover according to the chip and surface mount configuration of FIG. 25a above.

Referring to FIG. 29*a,* an LED chip module 2901 is depicted that has an array of LED chips 2902*a,* 2902*b,* etc located in a well 2903 of a heat sink 2904. Insulative covering 2910 as well as a cover or dome 2911 are provided respectively. The chips of FIG. 29a have insulative substrates.

Figure 29B:
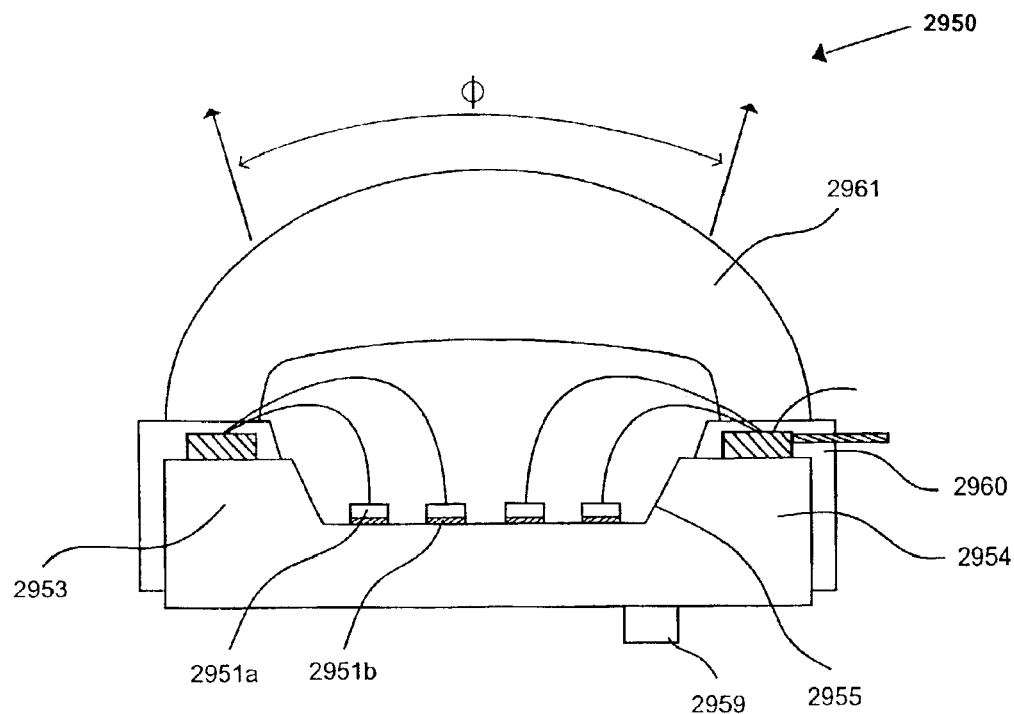
FIG. 29b depicts a light emitting surface mount chip package including array of chips, heat sink and protective dome, lens or cover according to the chip and surface mount configuration of FIG. 26a above.

Referring to FIG. 29b, an LED chip module 2950 is depicted that has an array of LED chips 2951a, 2951b, etc. located in a well 2955 of a heat sink 2954. Insulative covering 2960 as well as a cover or dome 2961 are provided respectively. The chips of FIG. 29b have conductive substrates and an electrode 2959 is provided on the heat sink.

Figure 30A:
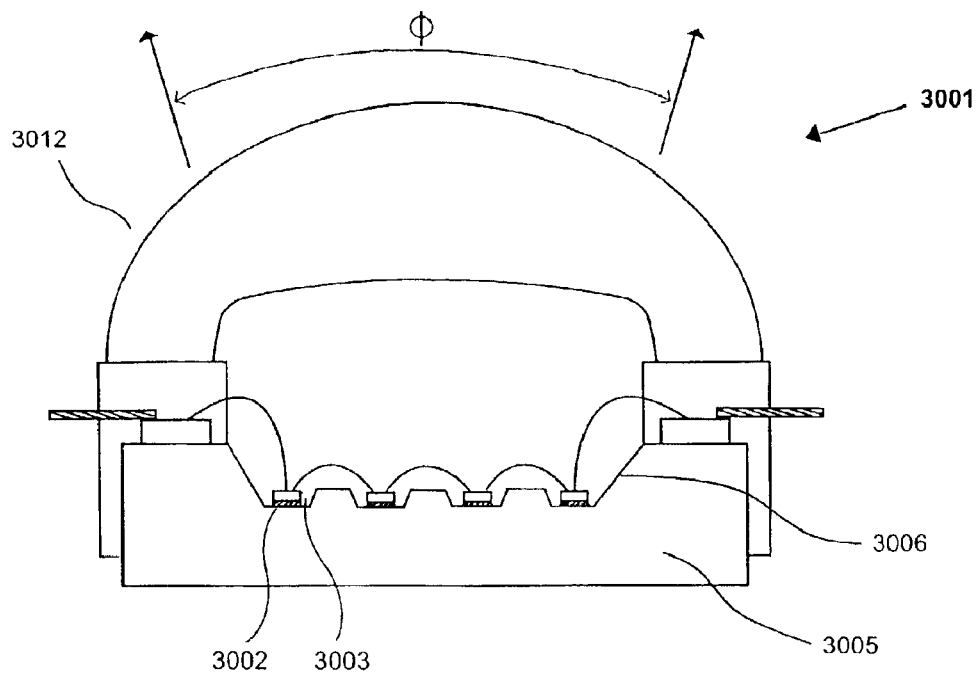
FIG. 30a depicts a light emitting surface mount chip package including array of chips in sub-wells, heat sink and protective dome, lens or cover according to the chip and surface mount configuration of FIG. 27a above.

Referring to FIG. 30a, an LED chip module 3001 is depicted that has an array of LED chips 3002, with each chip in a sub-well 3003 of a gross well 3006 of a heat sink 3005 and the entire module covered by a protective or focus dome 3012. The chips have electrically insulative substrates.

Figure 30B:
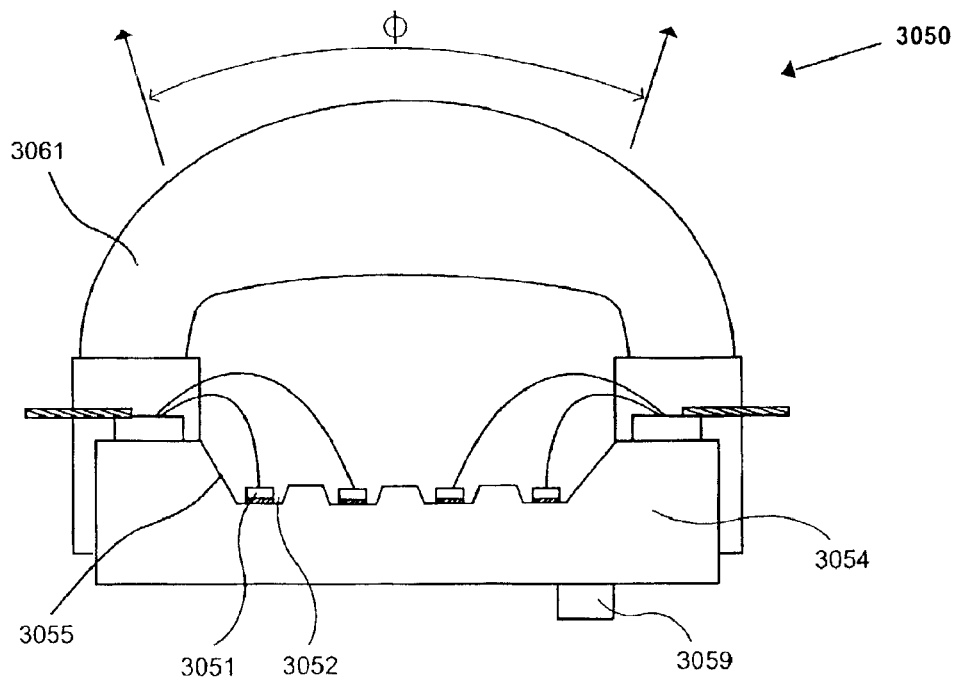
FIG. 30b depicts a light emitting surface mount chip package including array of chips in sub-wells, heat sink and protective dome, lens or cover according to the chip and surface mount configuration of FIG. 28a above.

Referring to FIG. 30b, an LED chip module 3050 is depicted that has an array of LED chips 3051, with each chip in a sub-well 3052 of a gross well 3055 of a heat sink 3054 and the entire module covered by a protective or focus dome 3061. The chips have electrically conductive substrates and there is an electrode 3056 on the heat sink.

Figure 31A:
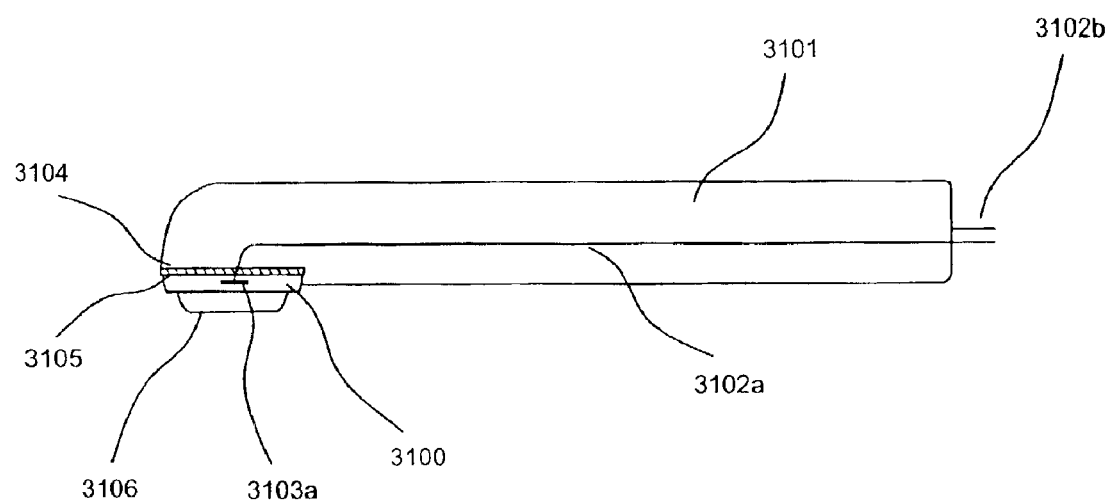
FIG. 31a depicts a side view of a single surface mount light emitting diode chip mounted to an elongate heat sink in a manner such that light from the chip is emitted at generally a 90 degree angle to the longitudinal axis of the elongate heat sink.
Figure 31B:
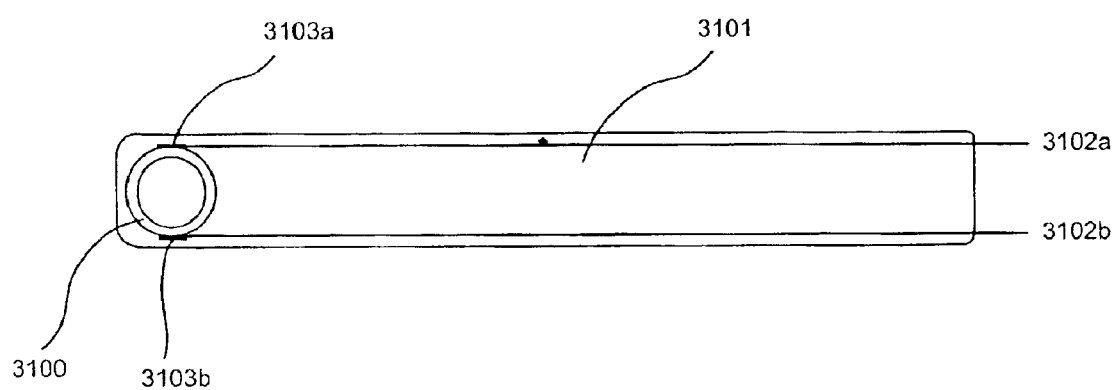

Referring to FIGS. 31a and 31b, side and bottom views of a surface mount chip configuration are depicted for mounting a single LED 3100 or LED module (as described previously) to an elongate heat sink 3101. Electrically conductive wires 3102a and 3102b and electrodes 3103a and 3103b are provided for powering the LED. The LED is mounted on a platform 3104 formed on the heat sink distal end. Mounting is achieved by use of light reflective and heat conductive adhesive 3105. A cover or focus dome 3106 is provided over the LED. The heat sink has a longitudinal axis, and the LED is mounted so that the average beam of light that it emits is generally at a 45 to 135 degree angle with that axis, and in some instances at a right angle to it.

Figure 32A:
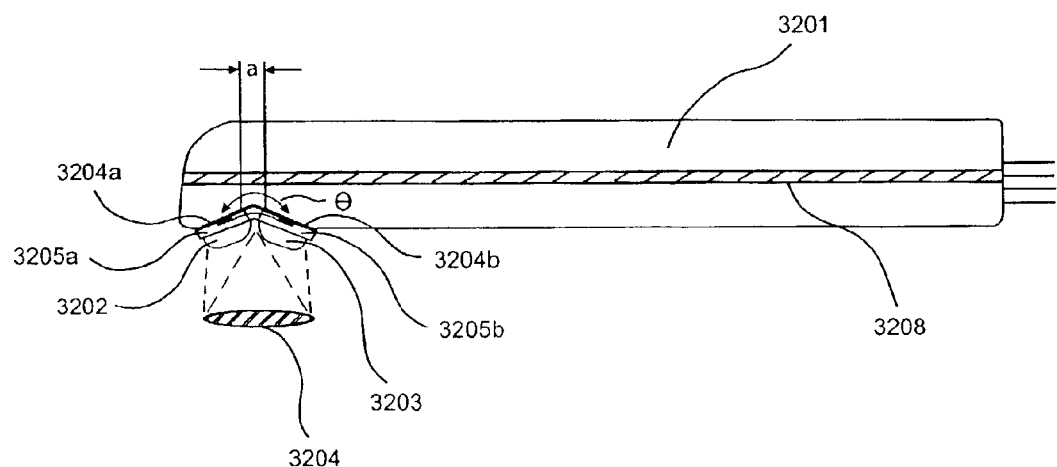
FIG. 32a depicts a cross-sectional side view of an elongate heat sink having two light emitting semiconductor chips in surface mount configuration in an angled orientation in order to present overlapping light beams for an enhanced density light footprint.
Figure 32B:
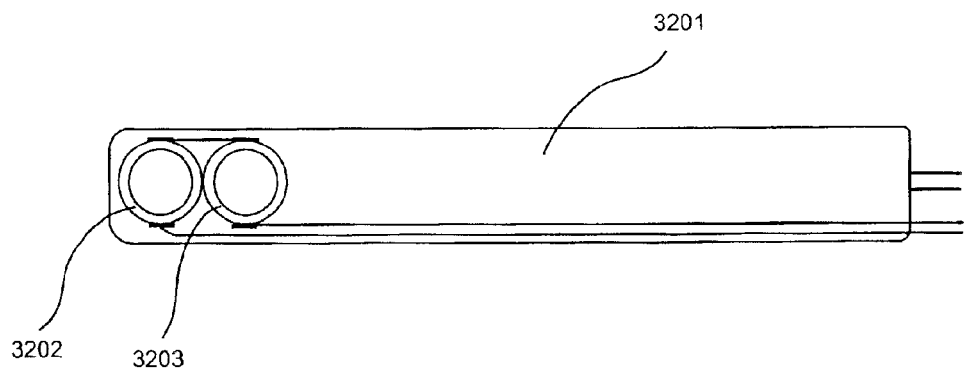

FIGS. 32a and 32b depict side and bottom views of an elongate heat sink 3201 having two light emitting semiconductor chips or modules 3202 and 3203 mounted on mounting platforms 3204a and 3204b using adhesive 3205a and 3505b (such as heat conductive or light reflective adhesive). The chips are mounted on the heat sink in an angled orientation with respect to each other in order to present overlapping light beams for an enhanced density light footprint 3204. The angle of orientation of the chips is depicted as θ which can be from zero to 180 degrees, or from 30 to 150 degrees, or from 45 to 135 degrees, or from 70 to 110 degrees, or from 80 to 100 degrees or about 90 degrees, as desired. The chips are offset from each other by a desired distance 'a', which can range from zero to any desired distance. Wires and electrodes are provided to power the LED's. An optional thermoelectric cooler 3208 may be provided to enhance heat removal.

Figure 33A:
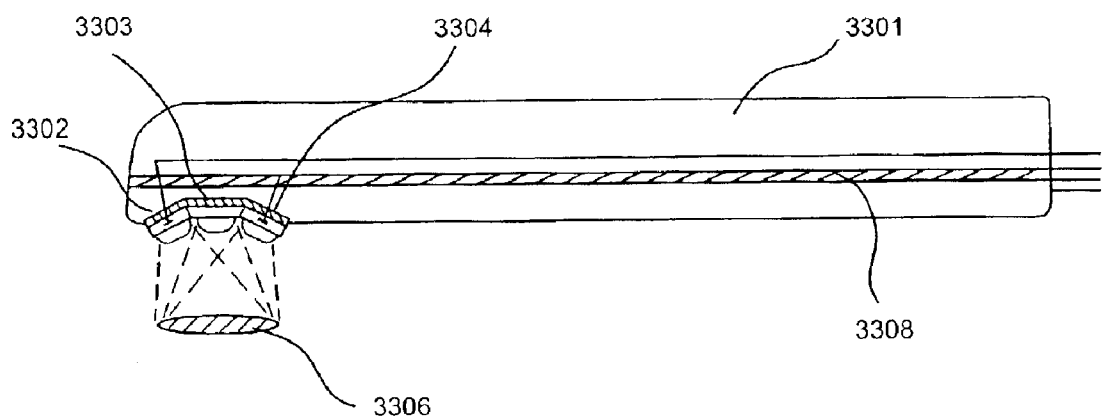
FIG. 33a depicts a cross-sectional side view of an elongate heat sink having three light emitting semiconductor chips mounted on it in an angled orientation in order to present overlapping light beams for an enhanced density light footprint.
Figure 33B:
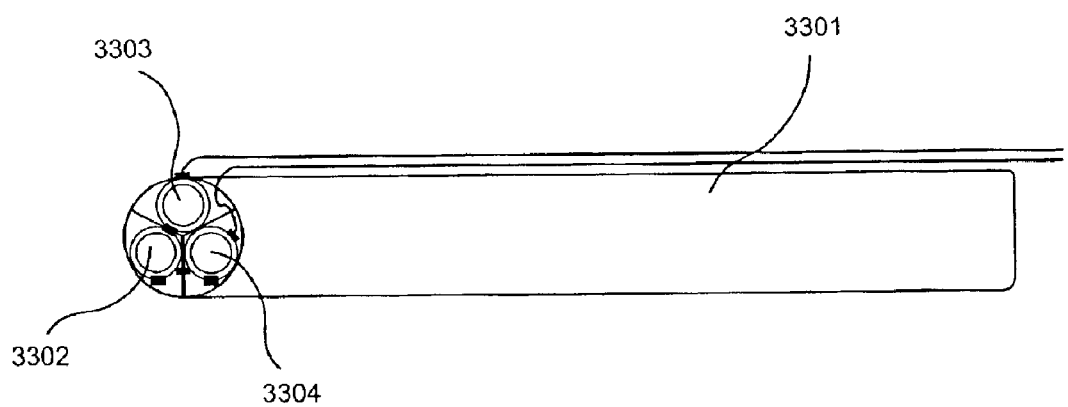
Figure 33C:
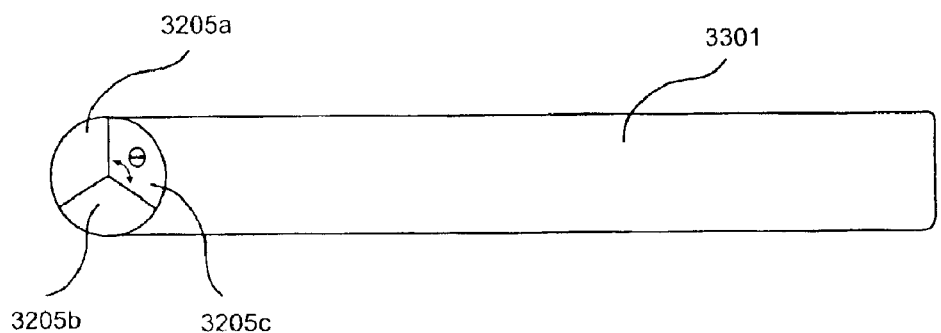
FIG. 33c depicts a bottom view of the heat sink of FIG. 33a and 33b to permit the reader to understand the angular orientation of the light emitting semiconductor chips.
Figure 33D:
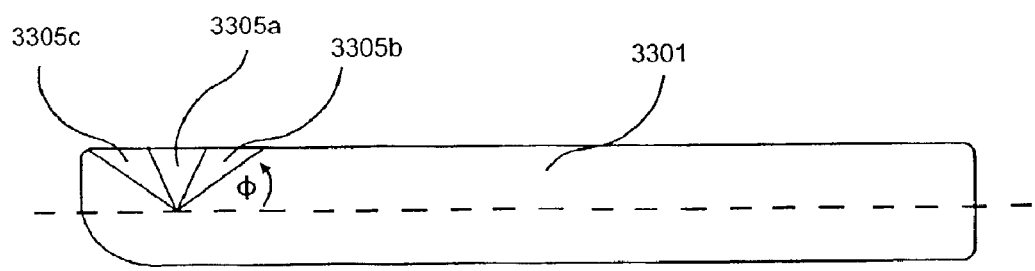
FIG. 33d depicts a side view of the heat sink for 3 surface mounted LED's.

FIG. 33a depicts a cross-sectional side view of a light module that uses three light emitting chips or chip modules. FIG. 33b depicts a bottom view of the same. FIG. 33c depicts a bottom view of the heat sink and mounting platform arrangement. FIG. 33d depicts a side view of the heat sink and mounting platform arrangement. An elongate heat sink 3301 is provided having three light emitting semiconductor chips or modules 3302, 3303, and 3304 mounted on mounting platforms in an angled orientation with respect to each other in order to present overlapping light beams for an enhanced density light footprint 3306. The mounting platforms depicted are generally planar and are arranged to present the densest useful light footprint. The modules may each include their own primary heat sink. The modules or chips may be mounted to the elongate heat sink using a heat conductive or light reflective adhesive as desired. Electrical wires and electrodes are used to power the chips or modules. An optional thermoelectric cooler 3308 may be provided. The mounting platforms 3305a, 3305b and 3305c can be seen more clearly in FIGS. 33c and 33d. The mounting platforms depicted are arranged in circular fashion at an angular offset θ with respect to each other, which in this case is 120 degrees. More mounting platforms could be used, and any desired arrangement of the mounting platforms could be accommodated. In FIG. 33d it can be seen that the mounting platforms 3305a, 3305b and 3305c are arranged at an angle φ with the longitudinal axis of the heat sink 3301. The angle φ can be from 0 to 90 degrees, from 10 to 80 degrees, from 20 to 70 degrees, from 30 to 60 degrees, from 40 to 50 degrees, or about 45 degrees as desired to generate the densest usable light footprint.

Figure 34A:
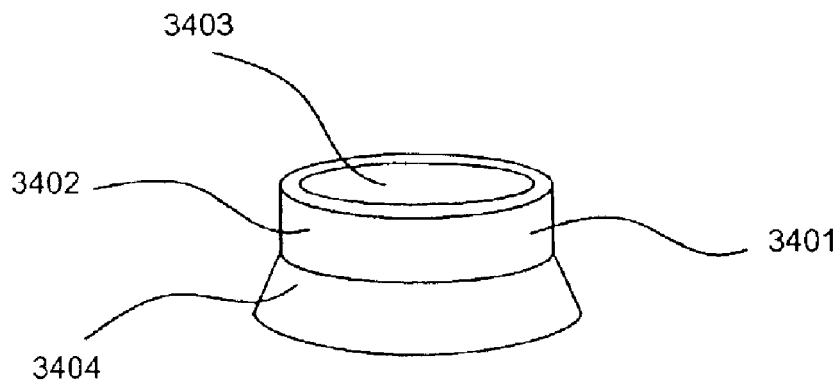
FIG. 34a depicts a light shield which may be used in conjunction with curing lights of the invention to shield human eyes from light emitting by the curing light.

FIG. 34a depicts a light shield 3401 which may be used in conjunction with curing lights of the invention to shield human eyes from light emitting by the curing light. The light shield includes an orifice 3403 through which light from a curing light may pass, the receptacle 3403 being formed by the light shield body 3402. A flare 3404 of the shield performs most of the protective function.

Figure 34B:
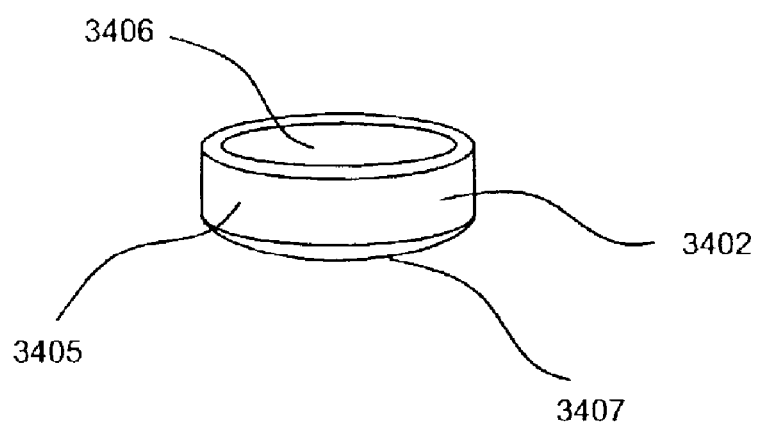
FIG. 34b depicts a focus lens which may be used to focus light emitted by curing lights of the invention in order to present a denser light footprint.

FIG. 34b depicts a focus lens 3402 which may be used to focus light emitted by curing lights of the invention in order to present a denser light footprint. The focus lens has an outer periphery 3405, a light entrance side 3506 and a light exit 3507. The focus lens may be designed according to known optical principles to focus light output from chips which may not be in an optimal pattern for use in curing.

Figure 34C:
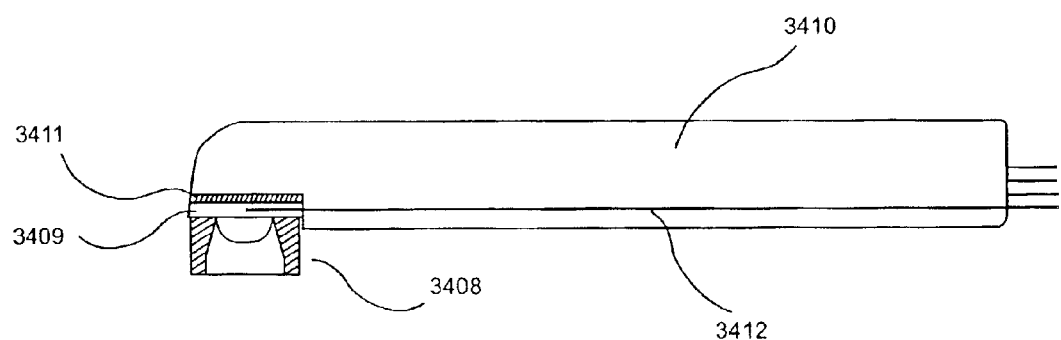
FIG. 34c depicts a light module with reflective cone installed.

FIG. 34c depicts a reflection cone 3408 in conjunction with LED module 3409, which is mounted on a heat sink 3910 by using heat conductive adhesive 3411. One or more connection wires 3412 may be provided to power the LED module 3409. The purpose of the light reflective cone is to re-shape the light beam from the LED module to create a light footprint of desired size and density. The inner wall of the cone 3408 may be coated with a highly reflective material, such as the reflective materials mentioned elsewhere in this document. The light beam from the LED module will change its path and configuration due to being reflected by the cone 3408.

Figure 34D:
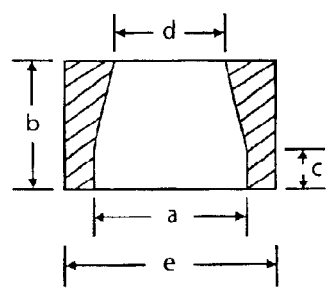
FIG. 34d depicts a reflective cone.

A detailed depiction of the light reflective cone 3408 is provided in FIG. 34d, which illustrates a cross-sectional view of the cone. An opening with an appropriate diameter "a" is provided at the proximal side of the cone for fitting to a light module of a curing light. The diameter "a" is chosen as an appropriate size for permitting light to enter therein. The cone has a total length "b". Adjacent light entrance at "a", a cylindrical portion of the cone is provided having a longitudinal length "c". Following cylindrical portion "c", there is a frusto-conical section of the cone interior having a length "b" minus "c". A light exit is provided at the end of the cone opposite the light inlet. The light exit has a diameter "d", where in many embodiments of the invention, "d" will be smaller than "a". The exterior diameter of the cone at its point of attachment to a light module is "e", where "e" is greater than "a". As desired, the various dimensions of the cone as well as its basic geometry (such as conical, frusto-conical, cylindrical, parabolic, etc.) are selected to achieve a desired light footprint size and density. Preferably, at least some portion of the interior surfaces of the reflective cone will have the ability to reflect light to aid in increasing the density of a light footprint. Appropriate reflective surfaces are mentioned elsewhere herein. Example dimensions of the various portions of the reflective cone in one embodiment of the invention are as follow: a=from about 5 mm to about 8 mm; b=from about 5 mm to about 8 mm; c=from about 2 mm to about 3 mm; d=from about 4 mm to about 6 mm; e=from about 8 mm to about 10 mm. Actual structure and dimensions of a reflective cone or reflective attachment or light exit for a curing light may vary depending on product type and application and design choice.

Figure 35:
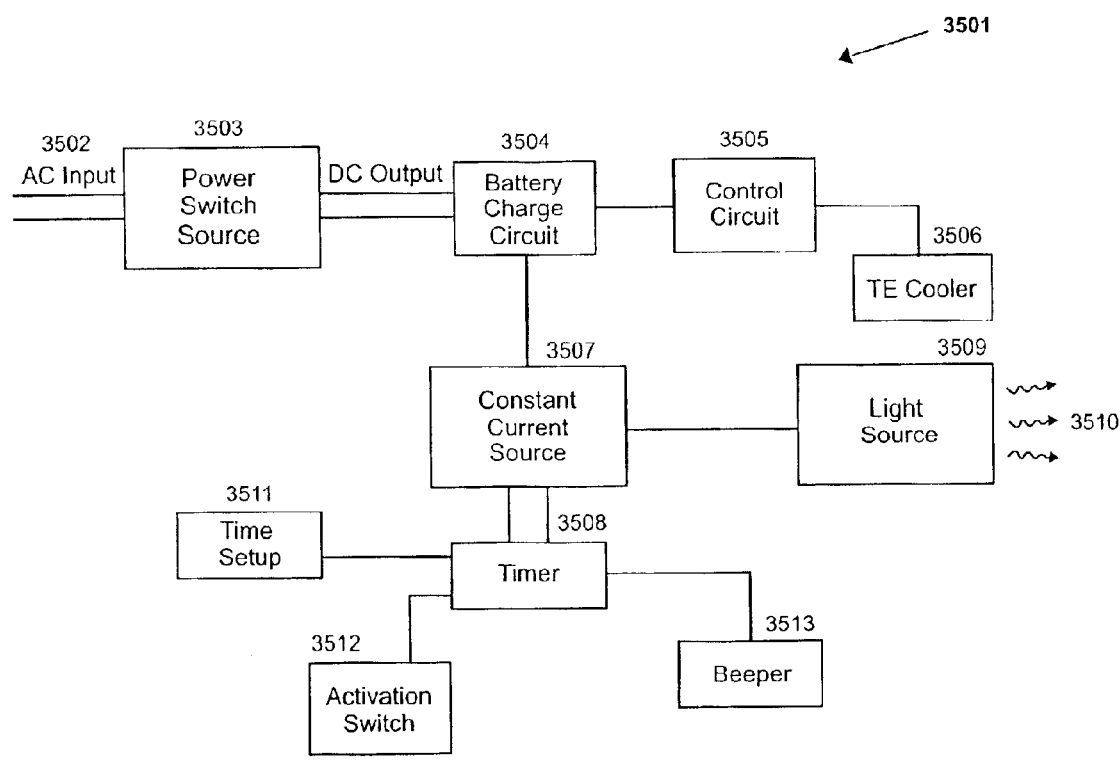
FIG. 35 depicts a block diagram of control circuitry that may be used with the embodiments of the inventions that utilize AC power.

FIG. 35 depicts a logic diagram 3501 of circuitry that may be used by AC-powered versions of the invented curing lights. AC power input 3502 is provided to a power switch source 3503 which outputs DC power to a main switch 3504. Main switch 3504 powers the control circuit 3505 and the optional TE cooler 3506 if so equipped. Main switch 3504 also provides a constant current source 3507 for the timer 3508, timer setup 3511, timer activation switch 3572 and optional light output beeper 3513. Constant current source 3507 also powers the light source 3509 to accomplish light output 3510.

Figure 36:
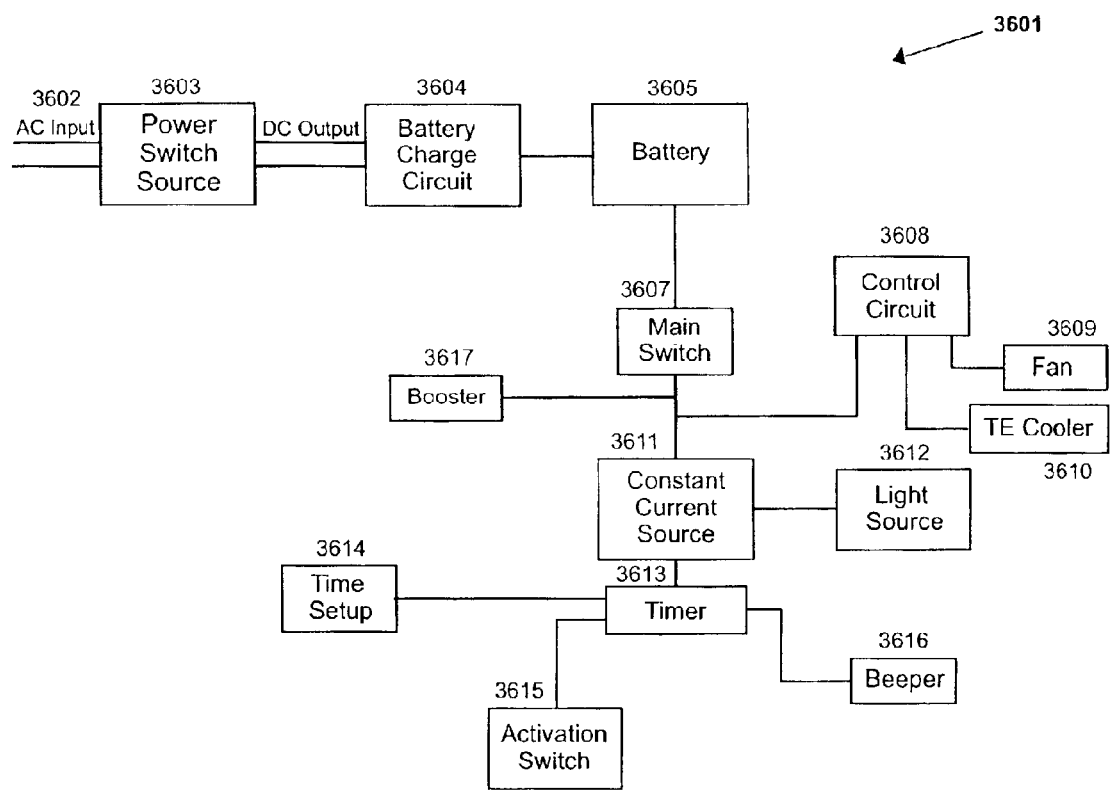
FIG. 36 depicts by a block diagram of control circuitry that may be used with the embodiments of the inventions that utilize battery power.

Referring to FIG. 36, a logic diagram 3601 of circuitry that may be used by battery-powered versions of the invented curing lights is depicted. AC power input 3602 is provided to a power switch source 3603 which outputs DC power to a battery charge unit 3604 that charges battery 3605. The battery 3605 powers main switch 3507. Main switch 3607 powers the control circuit 3608 that controls the optional TE cooler 3610 and the fan 3609. Main switch 3607 also provides a constant current source 3611 for the timer 3613, timer setup 3614, timer activation switch 3615 and optional light output beeper 3616. Constant current source 3611 also powers the light source 3612 to accomplish light output. An electrical voltage booster 3617 may be provided to increase the voltage from the battery to meet electrical requirements of the light source.

Figure 37:
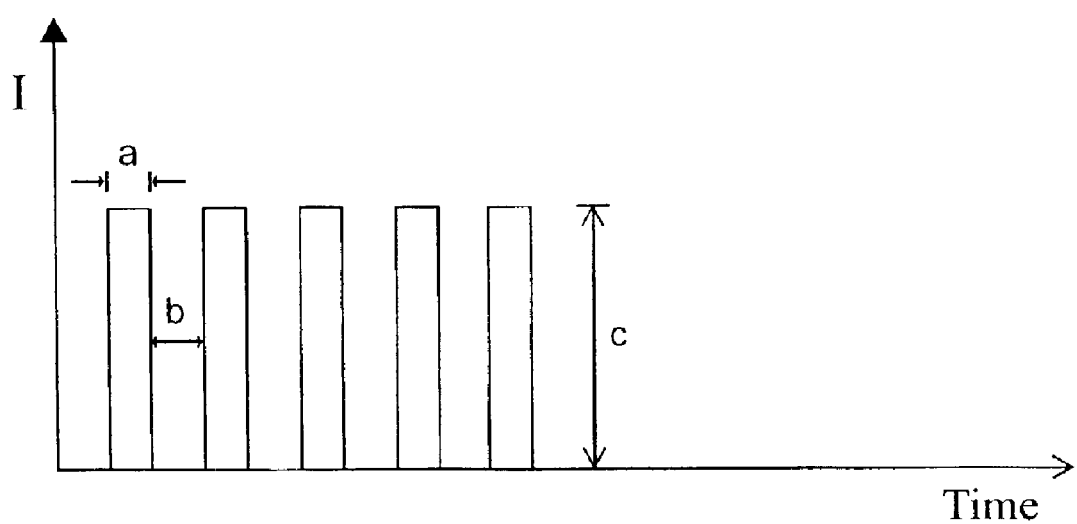
FIG. 37 depicts a graph of electrical current input I to the light emitting semiconductor chip(s) of the curing light versus time in a pulsed power input scheme in order to enhance light power output from the chip(s) and in order to avoid light intensity dimunition due to the heat effect.
Figure 38:
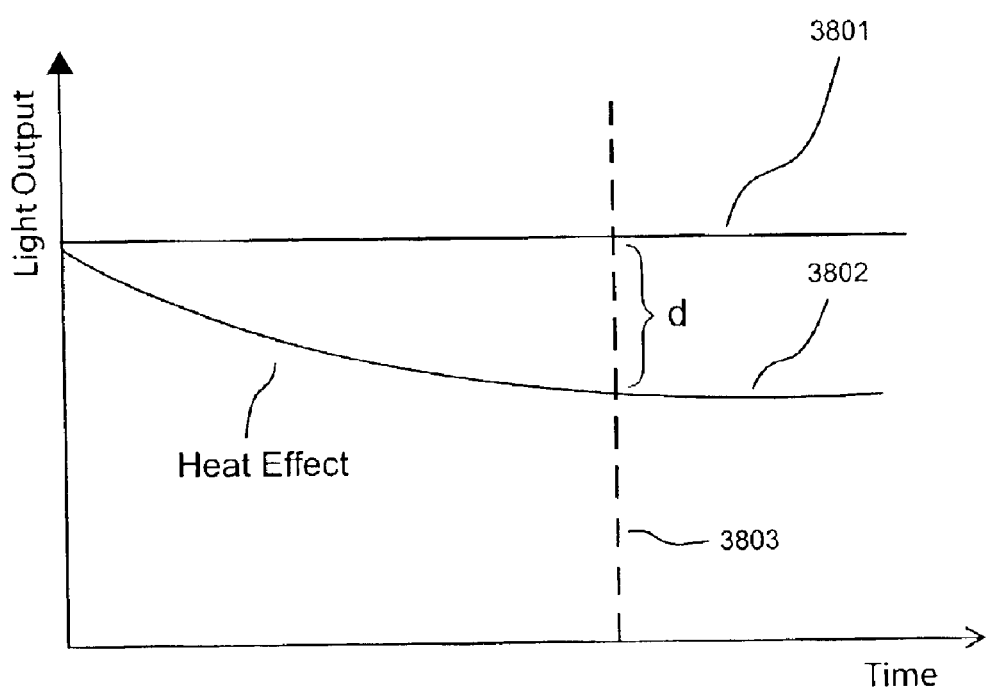
FIG. 38 depicts a graph of total light intensity output versus time in order to permit the reader to compare light intensity output when a current input pulsing scheme such as that of FIG. 37 is used to a traditional continuous wave current input approach which generates a heat effect is used.

Referring to FIG. 37, a graph of electrical current input I to the light emitting semiconductor chip(s) of the curing light versus time in a pulsed power input scheme is depicted. FIG. 38 depicts a graph of total light intensity output versus time in order to permit the reader to compare light intensity output when a current input pulsing scheme such as that of FIG. 37 is used to a traditional continuous wave current input approach which generates a heat effect is used. A pulsed current input scheme is used in order to enhance light power output from the chip(s) and in order to avoid light intensity reduction due to the heat effect. It has been found that when operated in continuous wave mode, the heat effect or heat buildup in the light emitting semiconductor chips will cause a decrease in light output intensity over time, until a stabilized light output yield is reached 3802 at point in time 3803. In contrast, when current input to the semiconductor light source is pulsed, a greater even level of light power output with greater intensity is achieved 3801. Laboratory experiments have shown this increase d to be more than 20% in some embodiments, providing significantly increased light yield and stable light intensity output in exchange for a simple control modification. Each of the square waves in FIG. 37 is a pulse of current input to the semiconductor light source, measured by "a=duration", "b=rest period", and "c=current input level (amps.)".

Examples of some heat sink materials which may be used in the invention include copper, aluminum, silicon carbide, boron nitride natural diamond, monocrystalline diamond, polycrystalline diamond, polycrystalline diamond compacts, diamond deposited through chemical vapor deposition and diamond deposited through physical vapor deposition. Any materials with adequate heat conductance can be used.

Examples of heat conductive adhesives which may be used are silver based epoxy, other epoxies, and other adhesives with a heat conductive quality. In order to perform a heat conductive function, it is important that the adhesive possess the following characteristics: (i) strong bonding between the materials being bonded, (ii) adequate heat conductance, (iii) electrically insulative or electrically conductive as desired (or both), and (iv) light reflective as desired, or any combination of the above. Examples of light reflective adhesives which may be used include silver and aluminum based epoxy.

Examples of substrates on which the semiconductors used in the invention may be grown include Si, GaAs, GaN, InP, sapphire, SiC, GaSb, InAs and others. These may be used for both electrically insulative and electrically conductive substrates.

Materials which may be used to used as a thermoelectric cooler in the invention include known semiconductor junction devices.

The semiconductor light source of the invention should emit light of a wavelength suitable to activate photoinitiators in the composite material to be cured.

Heat sinks used in this invention can be of a variety of shapes and dimensions, such as those depicted in the drawings or any others which are useful for the structure of the particular light source being constructed. It should be noted that particular advantage has been found when attaching the semiconductor light source to a small primary heat sink, and then the small primary heat sink is attached to an elongate secondary heat sink to draw heat away from the semiconductor and away from the patient's mouth.

While the present invention has been described and illustrated in conjunction with a number of specific embodiments, those skilled in the art will appreciate that variations and modifications may be made without departing from the principles of the invention as herein illustrated, described, and claimed.

The present invention may be embodied in other specific forms without departing from its spirit or essential characteristics. The described embodiments are to be considered in all respects as only illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A curing light comprising:

a wand adapted to be grasped by a human hand for use in positioning and manipulating the curing light, a longitudinal axis of said wand, a wand housing that is at least a portion of the exterior surface of said wand, said wand housing having a top, a bottom, a left side and a right side, a light emission control actuator which when actuated causes light to be emitted from the curing light, said light emission control actuator being located on said wand housing top, an elongate heat sink with a proximal end and a distal end, said proximal end being proximate said wand, said elongate heat sink having a longitudinal axis, said elongate heat sink being located at least partially within said housing a mounting platform located at said elongate heat sink distal end, said mounting platform being adapted to have a LED chip module, said mounting platform being located in a position that is on the same side of the curing light as said bottom of said wand housing, an LED chip module mounted on said mounting platform, said LED chip module including
- a primary heat sink, said primary heat sink having a smaller mass than said elongate heat sink,
- a well on said primary heat sink for mounting an LED chip,
- an LED chip mounted in said well,
- a cover that provides protective covering for said LED chip and which permits light emitted by said LED chip to pass through it to provide usable light exiting from said light module,
- said LED module being oriented so that light emitted by it is emitted generally from said wand housing bottom; and
- wherein light emitted by said LED chic module is emitted at an angle of from about 30 degrees to about 150 degrees to said wand longitudinal axis.

2. A curing light comprising:
- a wand adapted to be grasped by a human hand for use in positioning and manipulating the curing light,
- a wand housing that is at least a portion of the exterior surface of said wand, said wand housing having a top, a bottom, a left side and a right side,
- a light emission control actuator which when actuated causes light to be emitted from the curing light, said light emission control actuator being located on said wand housing top,
- an elongate heat sink with a proximal end and a distal end, said proximal end being proximate said wand, said elongate heat sink having a longitudinal axis, said elongate heat sink being located at least partially within said housing
- a mounting platform located at said elongate heat sink distal end, said mounting platform being adapted to have a LED chip module, said mounting platform being located in a position that is on the same side of the curing light as said bottom of said wand housing,
- an LED chip module mounted on said mounting platform, said LED chip module including
  - a primary heat sink, said primary heat sink having a smaller mass than said elongate heat sink,
  - a well on said primary heat sink for mounting an LED chip,
  - an LED chip mounted in said well,
  - a cover that provides protective covering for said LED chip and which permits light emitted by said LED chip to pass through it to provide usable light exiting from said light module,
- wherein light emitted by said LED chip module is emitted at an angle of from about 30 degrees to about 150 degrees to said elongate heat sink longitudinal axis.

3. A curing light comprising:
- a wand adapted to be grasped by a human hand for use in positioning and manipulating the curing light,
- a wand housing that is at least a portion of the exterior surface of said wand, said wand housing having a top, a bottom, a left side and a right side,
- a light emission control actuator which when actuated causes light to be emitted from the curing light, said light emission control actuator being located on said wand housing top,
- an elongate heat sink with a proximal end and a distal end, said proximal end being proximate said wand, said elongate heat sink having a longitudinal axis, said elongate heat sink being located at least partially within said housing
- a mounting platform located at said elongate heat sink distal end, said mounting platform being adapted to have a LED chip module, said mounting platform being located in a position that is on the same side of the curing light as said bottom of said wand housing,
- an LED chip module mounted on said mounting platform, said LED chip module including
  - a primary heat sink, said primary heat sink having a smaller mass than said elongate heat sink,
  - a well on said primary heat sink for mounting an LED chip,
  - an LED chip mounted in said well,
  - a cover that provides protective covering for said LED chip and which permits light emitted by said LED chip to pass through it to provide usable light exiting from said light module,
- wherein light emitted by said LED chip module is emitted at an angle of about 90 degrees to said elongate heat sink longitudinal axis.

* * * * *